(12) United States Patent
DeLuca et al.

(10) Patent No.: US 8,604,009 B2
(45) Date of Patent: Dec. 10, 2013

(54) (20S)-2-METHYLENE-19-NOR-22-DIMETHYL-1α,25-DIHYDROXYVITAMIN D₃ AND (20R)-2-METHYLENE-19-NOR-22-DIMETHYL-1α,25-HYDROXYVITAMIN D₃

(75) Inventors: Hector F. DeLuca, Deerfield, WI (US);
Agnieszka Flores, Madison, FL (US);
Pawel Grzywacz, Madison, WI (US);
Lori A. Plum, Arena, WI (US);
Margaret Clagett-Dame, Deerfield, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 259 days.

(21) Appl. No.: 13/053,844

(22) Filed: Mar. 22, 2011

(65) Prior Publication Data

US 2011/0237556 A1 Sep. 29, 2011

Related U.S. Application Data

(60) Provisional application No. 61/316,631, filed on Mar. 23, 2010.

(51) Int. Cl.
*A61K 31/593* (2006.01)
*C07C 401/00* (2006.01)

(52) U.S. Cl.
USPC ............................................ 514/167; 552/653

(58) Field of Classification Search
USPC ............................................ 514/167; 552/653
See application file for complete search history.

(56) References Cited

U.S. PATENT DOCUMENTS

| | | | |
|---|---|---|---|
| 5,086,191 A | 2/1992 | DeLuca et al. | |
| 5,246,925 A | 9/1993 | DeLuca et al. | |
| 5,536,713 A | 7/1996 | DeLuca et al. | |
| 5,585,369 A | 12/1996 | DeLuca et al. | |
| 5,587,497 A | 12/1996 | DeLuca et al. | |
| 5,843,928 A | 12/1998 | DeLuca et al. | |
| 5,936,133 A | 8/1999 | DeLuca et al. | |
| 5,945,410 A | 8/1999 | DeLuca et al. | |
| 6,384,087 B1 | 5/2002 | Zemel et al. | |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 6,774,251 B2 | 8/2004 | DeLuca et al. | |
| 6,806,262 B2 | 10/2004 | DeLuca et al. | |
| 6,835,723 B2 | 12/2004 | DeLuca et al. | |
| 6,844,330 B2 | 1/2005 | DeLuca et al. | |
| 6,844,331 B2 | 1/2005 | DeLuca et al. | |
| 6,844,332 B2 | 1/2005 | DeLuca et al. | |
| 6,844,457 B2 | 1/2005 | DeLuca et al. | |
| 6,846,811 B2 | 1/2005 | DeLuca et al. | |
| 6,887,860 B2 | 5/2005 | DeLuca et al. | |
| 6,890,914 B2 | 5/2005 | DeLuca et al. | |
| 6,894,037 B2 | 5/2005 | DeLuca et al. | |
| 6,939,868 B2 | 9/2005 | DeLuca et al. | |
| 6,992,074 B2 | 1/2006 | DeLuca et al. | |
| 7,053,075 B2 | 5/2006 | DeLuca et al. | |
| 7,056,904 B2 | 6/2006 | DeLuca et al. | |
| 7,064,115 B2 | 6/2006 | DeLuca et al. | |
| 7,071,179 B2 | 7/2006 | DeLuca et al. | |
| 7,094,774 B2 | 8/2006 | DeLuca et al. | |
| 7,094,916 B2 | 8/2006 | DeLuca et al. | |
| 7,112,579 B2 | 9/2006 | DeLuca et al. | |
| 7,115,594 B2 | 10/2006 | DeLuca et al. | |
| 7,141,558 B2 | 11/2006 | DeLuca et al. | |
| 7,205,286 B2 | 4/2007 | DeLuca et al. | |
| 7,208,484 B2 | 4/2007 | DeLuca et al. | |
| 7,214,670 B2 | 5/2007 | DeLuca et al. | |

(Continued)

FOREIGN PATENT DOCUMENTS

JP 3210156 9/1991
WO WO-98/41501 9/1998

(Continued)

OTHER PUBLICATIONS

Arbour, Nancy C. et al., "A Highly Sensitive Method for Large-Scale Measurements of 1,25-Dihydroxyvitamin D," *Analytical Biochemistry*, 1998, vol. 255, pp. 148-154.

Baggiolini et al., "Stereocontrolled Total Synthesis of 1α,25-Dihydroxyergocalciferol and 1α,25-Dihydroxyergocalciferol," *J. Org. Chem.*, (1986), vol. 51, pp. 3098-3108, published by American Chemical Society.

Casimir, D.A., et al., "cAMP Activates the Expression of Stearoly-CoA Desaturase Gene 1 during Early Preadipocyte Differentiation," *J. Biol. Chem.*, (1996), 271(47), pp. 29847-29853; The American Society for Biochemistry and Molecular Biology, Inc.

(Continued)

*Primary Examiner* — Barbara P Badio
(74) *Attorney, Agent, or Firm* — Foley & Lardner LLP

(57) ABSTRACT

Compounds of formula I are provided where $X^1$, $X^2$ and $X^3$ are independently selected from H or hydroxy protecting groups. Such compounds may be used in preparing pharmaceutical compositions and are useful in treating a variety of biological conditions.

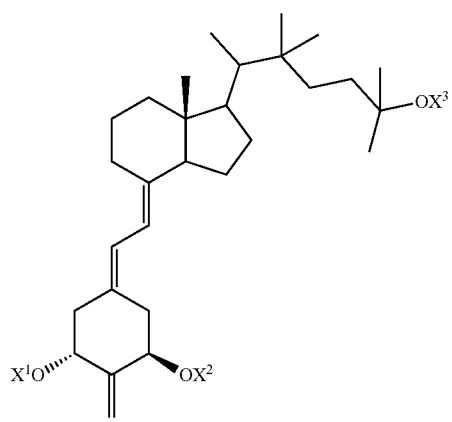

I

20 Claims, 8 Drawing Sheets

(56) References Cited

U.S. PATENT DOCUMENTS

| | | | |
|---|---|---|---|
| 7,214,671 B2 | 5/2007 | DeLuca et al. |
| 7,232,810 B2 | 6/2007 | DeLuca et al. |
| 7,238,681 B2 | 7/2007 | DeLuca et al. |
| 7,241,748 B2 | 7/2007 | DeLuca et al. |
| 7,241,749 B2 | 7/2007 | DeLuca et al. |
| 7,241,750 B2 | 7/2007 | DeLuca et al. |
| 7,241,751 B2 | 7/2007 | DeLuca et al. |
| 7,241,752 B2 | 7/2007 | DeLuca et al. |
| 7,241,909 B2 | 7/2007 | DeLuca et al. |
| 7,244,719 B2 | 7/2007 | DeLuca et al. |
| 7,300,925 B2 | 11/2007 | DeLuca et al. |
| 7,468,361 B2 | 12/2008 | DeLuca et al. |
| 7,511,030 B2 | 3/2009 | DeLuca et al. |
| 7,534,778 B2 | 5/2009 | DeLuca et al. |
| 7,541,348 B2 | 6/2009 | DeLuca et al. |
| 7,541,349 B2 | 6/2009 | DeLuca et al. |
| 7,563,783 B2 | 7/2009 | DeLuca et al. |
| 7,648,972 B2 | 1/2010 | DeLuca et al. |
| 7,648,973 B2 | 1/2010 | DeLuca et al. |
| 7,704,980 B2 | 4/2010 | DeLuca et al. |
| 7,704,981 B2 | 4/2010 | DeLuca et al. |
| 7,704,982 B2 | 4/2010 | DeLuca et al. |
| 7,713,951 B2 | 5/2010 | DeLuca et al. |
| 7,713,952 B2 | 5/2010 | DeLuca et al. |
| 7,718,636 B2 | 5/2010 | DeLuca et al. |
| 7,718,637 B2 | 5/2010 | DeLuca et al. |
| 7,718,638 B2 | 5/2010 | DeLuca et al. |
| 7,741,313 B2 | 6/2010 | DeLuca et al. |
| 7,741,314 B2 | 6/2010 | DeLuca et al. |
| RE41,474 E | 8/2010 | DeLuca et al. |
| RE41,491 E | 8/2010 | DeLuca et al. |
| 7,888,339 B2 | 2/2011 | DeLuca et al. |
| 7,893,043 B2 | 2/2011 | DeLuca et al. |
| 7,915,242 B2 | 3/2011 | DeLuca et al. |
| 2005/0065088 A1 | 3/2005 | Thompson |
| 2005/0065133 A1 | 3/2005 | Lee et al. |
| 2005/0065180 A1 | 3/2005 | Lee |
| 2005/0070512 A1 | 3/2005 | Lee |
| 2005/0119242 A1 | 6/2005 | DeLuca et al. |
| 2007/0219168 A1 | 9/2007 | DeLuca et al. |
| 2009/0170820 A1 | 7/2009 | DeLuca et al. |
| 2009/0227545 A1 | 9/2009 | DeLuca et al. |
| 2010/0009946 A1 | 1/2010 | DeLuca et al. |
| 2010/0009947 A1 | 1/2010 | DeLuca et al. |
| 2010/0160267 A1 | 6/2010 | DeLuca et al. |
| 2010/0179344 A1 | 7/2010 | DeLuca et al. |
| 2011/0034426 A1 | 2/2011 | DeLuca et al. |
| 2011/0059926 A1 | 3/2011 | DeLuca et al. |
| 2011/0086824 A1 | 4/2011 | DeLuca et al. |

FOREIGN PATENT DOCUMENTS

| | | |
|---|---|---|
| WO | WO-00/59513 | 10/2000 |
| WO | WO-02/17734 | 3/2002 |
| WO | WO-2005/027913 | 3/2005 |
| WO | WO-2005/027915 | 3/2005 |
| WO | WO-2005/027924 | 3/2005 |
| WO | WO-2005/027929 | 3/2005 |
| WO | WO-2005/027931 | 3/2005 |
| WO | WO-2006/057886 | 6/2006 |
| WO | WO-2006/119309 | 11/2006 |
| WO | WO-2009/026265 | 2/2009 |

OTHER PUBLICATIONS

Chomczynski, P. et al., "Single-Step Method of RNA Isolation by Acid Guanidinium Thiocyanate-Phenol-Chloroform Extration," *Anal. Biochem.*, (1987), 162, pp. 156-159; Academic Press, Inc.

Cohen, P. et al., "Role for Stearoyl-CoA Desaturase-1 in Leptin-Mediated Weight Loss," *Science* (2002), 297, pp. 240-243.

Collins et al., "Normal Functional Characteristics of Cultured Human Promyelocytic Leukemia Cells (HL-60) After Induction of Differentiation by Dimethylsulfoxide" *J. Exp. Med.*, (1979), 149, pp. 969-974.

Dame et al., "Monoclonal Antibodies to the Porcine Intestinal Receptor for 1,25-Dihydroxyvitamin D3: Interaction with Distinct Receptor Domains," *Biochemistry*, (1986); vol. 25, pp. 4523-4534; American Chemical Society.

Daniewski, A. R. et al., "A Novel Silylcopper Catalyst for the Reductive Bromination of Hajos Dione. Improved Preparation of a CD Synthon for the Synthesis of Vitamin D," *J. Org. Chem.*, (2001), 66, pp. 626-628; American Chemical Society.

DeLuca, H. F., "Applications of New Vitamin D. Compounds to Disease," *DN&P*, (Mar. 1992), vol. 5, No. 2, pp. 87-92.

Grzywacz, P. et al., "Methyl substitution of the 25-hydroxy group on 2-methylene-19-nor-1α,25-dihydroxyvitamin D3 (2MD) reduces potency but allows bone selectivity", *Biochemistry*, (2007), vol. 460, pp. 274-284, Elsevier Inc.

Hanessian et al., "Total Synthesis of (−)-Reserpine Using the Chiron Approach," *J. Org. Chem.*, 62, (1997), pp. 465-473; American Chemical Society.

International Search Report and Written Opinion for Intl. Pat. Appln. No. PCT/US2010/058208, mailed on Feb. 10, 2011, 12 pp.

Kutner et al., "Novel Convergent Synthesis of Side-Chain-Modified Analogues of 1α,25-Dihydroxycholecalciferol and 1α,25-Dihydroxyergocalciferol," *J. Org. Chem.*, (1988), vol. 53, pp. 3450-3457; American Chemical Society.

Lythgoe et al., "Calciferol and its Relatives. Part 22. A direct total Synthesis of Vitamin D2 and Vitamin D3," *J. Chem. Soc. Perkin I*, (1978), pp. 590-595.

Lythgoe, "Synthetic Approaches to Vitamin D and its Relatives," *Chem. Soc. Rev.*, (1983), vol. 9, pp. 449-475.

Mascareñas et al., "Studies on the Synthesis of Side-Chain Hydroxylated Metabolites of Vitamin D. 3. Synthesis of 25-Ketovitamin D3 and 25-Hydroxyvitamin D3," *J. Org. Chem.*, vol. 51, pp. 1269-1272 (1986); American Chemical Society.

Mincione et al., "Improved Conversion of Vitamin D2 into the Windaus Ketone and its Regioselective Hydroxylation via Organoboranes at C26," *Synth. Commun.*, vol. 19(5&6), pp. 723-735 (1989).

Miyamoto et al., "Synthetic Studies of Vitamin D Analogues. XIV. Synthesis and Calcium Regulating Activity of Vitamin D3 Analogues Bearing a Hydroxyalkoxy Group at the 20A-Position," *Chem. Pharm. Bull.*, vol. 41(6), pp. 1111-1113 (1993); Pharmaceutical Society of Japan.

Nishii et al., "The Development of Vitamin D3 Analogues for the Treatment of Osteoporosis," *Osteoporosis Int. Suppl.*, vol. 1, 190-193 (1993); European Foundation for Osteoporosis.

Okano et al., "Regulatory Activities of 20A-(3-Hydroxypropoxy)-1α, 25-Dihydroxy-Vitamin D3, a Novel Synthetic Vitamin D3 Derivative, on Calcium Metabolism," *Biochem. Biophys. Res. Commun.*, vol. 163(3), pp. 1444-1449 (1989); published by Academic Press, Inc.

Ostrem et al., "24- and 26-homo-1,25-dihydroxyvitamin D3: Preferential activity in inducing differentiation of human leukemia cells HL-60 in vitro," *Proc. Natl. Acad. Sci. USA*, vol. 84, pp. 2610-2614 (1987).

Ostrem et al., "Induction of Monocytic Differentiation of HL-60 Cells by 1,25-Dihydroxyvitamin D Analogs," *J. Biol. Chem.*, vol. 262(29), pp. 14164-14171 (1987); The American Society for Biochemistry and Molecular Biology, Inc.

Peleg, S., Chapter 60: Molecular Basis for Differential Action of Vitamin D Analogs, in: Vitamin D, Feldman, *Glorieux and Pike* (eds.), pp. 1011-1025 (1997); Academic Press.

Perlman et al., "1α,25-Dihydroxy-19-Nor-Vitamin D3, A Novel Vitamin D-Related Compound with Potential Therapeutic Activity," *Tetrahedron Lett.*, vol. 31(13), pp. 1823-1824 (1990); Pergamon Press, Great Britain.

Perlman et al., "Novel Synthesis of 19-Nor-Vitamin D Compounds," *Tetrahedron Lett.*, vol. 32(52), pp. 7663-7666 (1991); Pergamon Press, Great Britain.

Peterson et al., "Studies of the Ketone Obtained from the Ozonolysis of Vitamin D. Molecular Mechanics Calculations for It and Related Hydrindanones," *J. Org. Chem.*, vol. 51, pp. 1948-1954 (1986); American Chemical Society.

(56) References Cited

OTHER PUBLICATIONS

Plum, L. A. et al., "Biologically active noncalcemic analogs of 1a,25-dihydroxyvitamin D with an abbreviated side chain containing no hydroxyl," *Proc. Natl. Acad. Sci. USA*, 101(18), pp. 6900-6904 (2004).
Posner et al., "2-Fluoroalkyl A-Ring Analogs of 1,25-Dihydroxyvitamin D3 Stereocontrolled Total Synthesis via Intramolecular and Intermolecular Diels 013 Alder Cycloadditions. Preliminary Biological Testing," *J. Org. Chem.*, vol. 60, pp. 4617-4628 (1995); American Chemical Society.
Posner et al., "Stereocontrolled Total Synthesis of Calcitriol Derivatives: 1,25-Dihydroxy-2(4019-hydroxybutyl)vitamin D3 Analogs of an Osteoporosis Drug," *J. Org. Chem.*, vol. 59, pp. 7855-7861 (1994); American Chemical Society.
Qiu, Z. et al., "DNA Synthesis and Mitotic Clonal Expansion is Not a Required Step for 3T3-L1 Preacipocyte Differentiation into Adipocytes," *J. Biol. Chem.*, 276(15), pp. 11988-11995 (2001); The American Society for Biochemistry and Molecular Biology, Inc.
Sakuma, T. et al., "Inhibition of Peroxisome Proliferator-activated Receptor 1a Signaling by Vitamin D Receptor," *Biochem. Biophys. Res. Commun.*, vol. 312, pp. 513-519 (2003).
Sardina et al., "Studies on the Synthesis of Side-Chain Hydroxylated Metabolites of Vitamin D. 2. Stereocontrolled Synthesis of 25-Hydroxyvitamin D2," *J. Org. Chem.*, vol. 51, 1264-1269 (1986); American Chemical Society.
Sato, M. et al., "Demonstration of 1a,25-Dihydroxyvitamin D3 Receptor-Like Molecule in ST 13 and 3T3 L1 Preadipocytes and its Inhibitory Effects on Preadipocyte Differentiation,"*J. Cell. Phys.*, 135, pp. 545-550 (1988); Alan R. Liss, Inc.
Shi et al., "1a,25-Dihydroxyvitamin D3 modulates human adipocyte metabolism via nongenomic action," *The FASEB Journal* (Dec. 2001), vol. 15, pp. 2751-2753.
Sicinski, R. R. et al., "New 1a,25-Dihydroxy-19-norvitamin D3 Compounds of High Biological Activity: Synthesis and Biological Evaluation of 2-Hydroxymethyl, 2-Methyl, and 2-Methylene Analogues," *J. Med. Chem.*, 41, pp. 4662-4674 (1998); American Chemical Society.
Sicinski, R. R. et al., "Synthesis and Biological Activity of 2-Hydroxy and 2-Alkoxy Analogs of 1a,25-Dihydroxy-19-norvitamin D3," *J. Med. Chem.*, 37, pp. 3730-3738 (1994); American Chemical Society.
Silverman, R.B., *The Organic Chemistry of Drug Design and Drug Action*, 2nd Edition, (2004), ISBN: 0-12-643732-7, Title/Cover, 1 page, Contents, 1 page, pp. 26-28, and Publication Information, 1 page; Elsevier Academic Press, U.S.A.
Suda, T. et al., "Biological Activity of 25-Hydroxyergocalciferol in Rats," *J. Nutrition*, vol. 100, pp. 1049-1052 (1970).
Toh et al., "Studies on a Convergent Route to Side-Chain Analogues of Vitamin D: 25-Hydroxy-23-oxavitamin D3," *J. Org. Chem.*, 48, pp. 1414-1417 (1983); American Chemical Society.
Xue et al., "Mechanism of intracellular calcium ([Ca2+]i) inhibition of lipolysis in human adipocytes," *The FASEB Journal* (Nov. 17, 2001), vol. 15, pp. 2527-2529.
International Search Report & Written Opinion for Intl. Pat. Appln. No. PCT/US2011/029432, mailed on Jul. 14, 2011, 11 pp.
Sakamaki, Y. et al., "Potent antagonist for the vitamin D receptor: vitamin D analogues side chain structure", *J. Med. Chem.*, Jul. 7, 2010, vol. 53, 7, pp. 5813-5826.
Binderup, Lise et al., "Effects of a Novel Vitamin D Analogue MC903 on Cell Proliferation and Differentiation In Vitro and on Calcium Metabolism In Vivo," Biochemical Pharmacology, (1988), vol. 37, No. 5, pp. 889-895.
Campbell, Moray J. et al., "Toward Therapeutic Intervention of Cancer by Vitamin D Compounds," Journal of the National Cancer Institute, (Feb. 5, 1997), vol. 89, No. 3, pp. 182-185.
Cantorna, Margherita T. et al., "1,25 Dihydroxyvitamin $D_3$ Reversibly Blocks the Progression of Relapsing Encephalomyelitis, A Model of Multiple Sclerosis," Proc. Natl. Acad. Sci. USA, (Jul. 1996), vol. 93, pp. 7861-7864.
Gallagher, J.C. et al., "Effects of Calcitriol in Osteoporosis," Osteoporosis: Recent Advanced in Pathogenesis and Treatment, University Park Press, Baltimore, Maryland, (1981), pp. 419-423.
Gallagher, J.C. et al., "Intestinal Calcium Absorption and Serum Vitamin D Metabolites in Normal.Subjects and Osteoporotic Patients: Effect of Age and Dietary Calcium," J. Clin. Invest., (Sep. 1979), vol. 64, pp. 729-736.
Geilen, Christoph et al., "The Vitamin $D_3$ Analogue, Calcipotriol, Induces Sphingomyelin Hydrolysis in Human Keratinocytes," FEBS Letters, (1996), vol. 378, pp. 88-92.
Munker, Reinhold et al., "A New Series of Vitamin D Analogs is Highly Active for Clonal Inhibition, Differentiation, and Induction of WAF1 in Myeloid Leukemia," Blood, (Sep. 15, 1996), vol. 88, No. 6, pp. 2201-2209.
Rebel, Vivienne I. et al., "Monocytic Differentiation Induction of HL-60 Cells by MC 903, A Novel Vitamin D Analogue," Leukemia Research, (1992), vol. 16, No. 5, pp. 443-451.
Shiraki, Masataka et al., "Long-Term Treatment of Postmenopausal Osteoporosis with Active Vitamin $D_3$, 1-α-Hydroxycholecalciferol (1α-OHD$_3$) and 1,24 Dihydroxycholecalciferol (1,24(OH)$_2$D$_3$)," Endocrinol. Japon., (Apr. 1985), 32(2), pp. 305-315.

(20S)-2-METHYLENE-19-NOR-22-DIMETHYL-1α,25-DIHYDROXYVITAMIN $D_3$ AND (20R)-2-METHYLENE-19-NOR-22-DIMETHYL-1α,25-HYDROXYVITAMIN $D_3$

CROSS REFERENCE TO RELATED APPLICATIONS

This application claims priority to U.S. Provisional Application No. 61/316,631 filed Mar. 23, 2010, the entire disclosure of which is hereby incorporated by reference and for all purposes in its entirety as if fully set forth herein.

FIELD

This present technology relates to vitamin D compounds, and more particularly to (20S)-2-methylene-19-nor-22-dimethyl-1α,25-dihydroxyvitamin $D_3$ and (20R)-2-methylene-19-nor-22-dimethyl-1α,25-dihydroxyvitamin $D_3$ and derivatives thereof, and to pharmaceutical formulations that include this compound. The present technology also relates to the use of these compounds in the treatment of various diseases and in the preparation of medicaments for use in treating various diseases.

BACKGROUND

The natural hormone, 1α,25-dihydroxyvitamin $D_3$ (also referred to as 1α,25-dihydroxycholecalciferol and calcitriol) and its analog in the ergosterol series, i.e. 1α,25-dihydroxyvitamin $D_2$, are known to be highly potent regulators of calcium homeostasis in animals and humans, and their activity in cellular differentiation has also been established, Ostrem et al., *Proc. Natl. Acad. Sci. USA*, 84, 2610 (1987). Many structural analogs of these metabolites have been prepared and tested, including 1α-hydroxyvitamin $D_3$, 1α-hydroxyvitamin $D_2$, various side chain homologated vitamins, and fluorinated analogs. Some of these compounds exhibit an interesting separation of activities in cell differentiation and calcium regulation. This difference in activity may be useful in the treatment of a variety of diseases such as renal osteodystrophy, vitamin D-resistant rickets, osteoporosis, psoriasis, and certain malignancies. The structure of 1α,25-dihydroxyvitamin $D_3$ and the numbering system used to denote the carbon atoms in this compound are shown below.

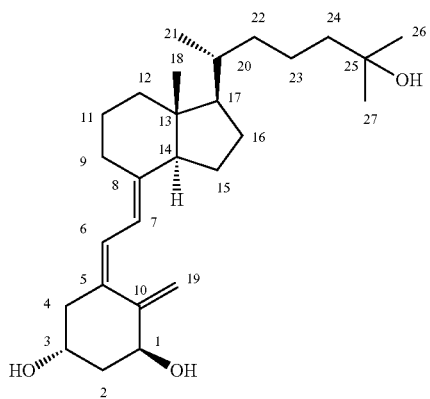 [SMILES: C=C1/C(=C\C(C)=C2/CCC[C@]3(C)[C@@H]([C@H](C)CCCC(C)(C)O)CC[C@@H]23)C[C@@H](O)C[C@@H]1O]

1α,25-Dihydroxyvitamin $D_3$=1α,25-Dihydroxycholecalciferol=Calcitriol

SUMMARY

The present technology provides (20R)-2-methylene-19-nor-22-dimethyl-1α,25-dihydroxyvitamin $D_3$ and (20S)-2-methylene-19-nor-22-dimethyl-1α,25-dihydroxyvitamin $D_3$ and related compounds, pharmaceutical formulations that include (20S)-2-methylene-19-nor-22-dimethyl-1α,25-dihydroxyvitamin $D_3$ or (20R)-2-methylene-19-nor-22-dimethyl-1α,25-dihydroxyvitamin $D_3$, methods of treating various disease states using this compound, and the use of this compound in the preparation of medicaments for treating various disease states.

Therefore, in one aspect, the present technology provides a compound having the formula I shown below

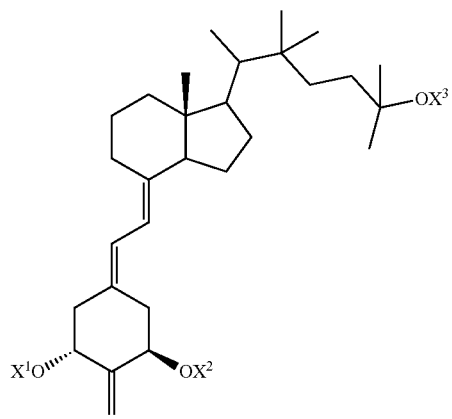

where $X^1$, $X^2$ and $X^3$ may be the same or different and are independently selected from H or hydroxy-protecting groups. In some embodiments, the carbon at position 20 has the S-configuration as shown in the compound of formula IA and in others it has the R-configuration as shown in the compound of formula IB:

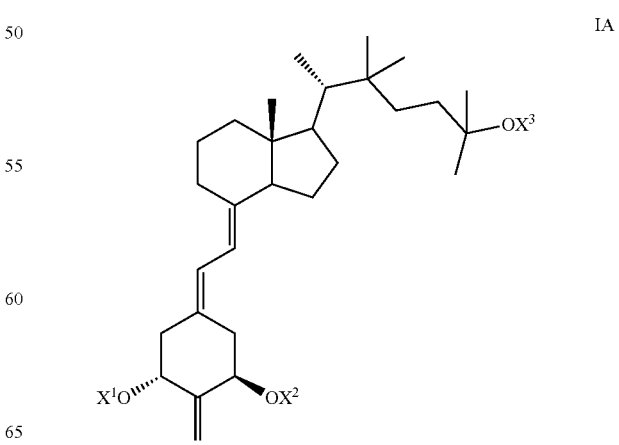

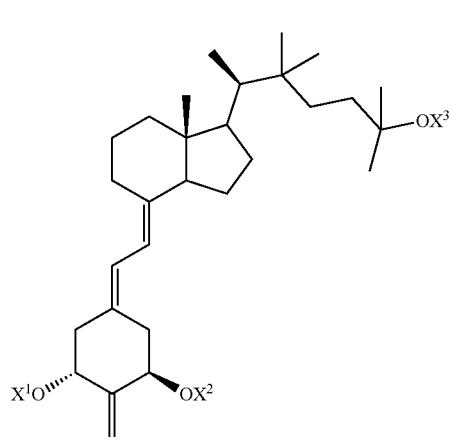

IB

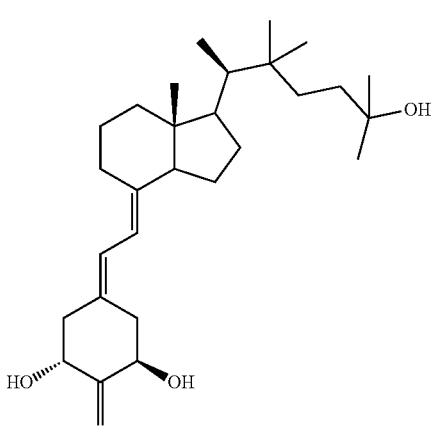

IIB

In some embodiments of compounds of formulas I, IA, or IB, $X^1$, $X^2$ and $X^3$ are both hydroxy protecting groups such as silyl groups. In some such embodiments, $X^1$ and $X^2$ are both t-butyldimethylsilyl groups and $X^3$ is a triethylsilyl group.

In some embodiments, the compound has the formula II.

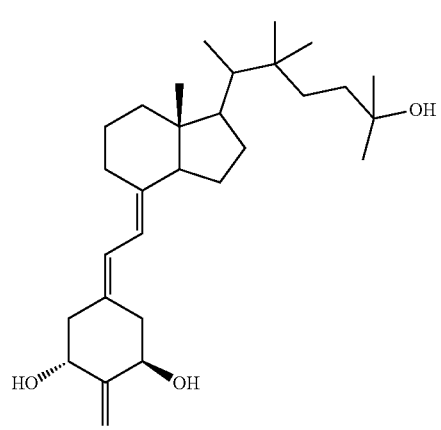

II

In some embodiments, the compound is (20S)-2-methylene-19-nor-22-dimethyl-1α,25-dihydroxyvitamin $D_3$ having the formula IIA as shown below or the compound is (20R)-2-methylene-19-nor-22-dimethyl-1α,25-dihydroxyvitamin $D_3$ having the formula IIB as shown below:

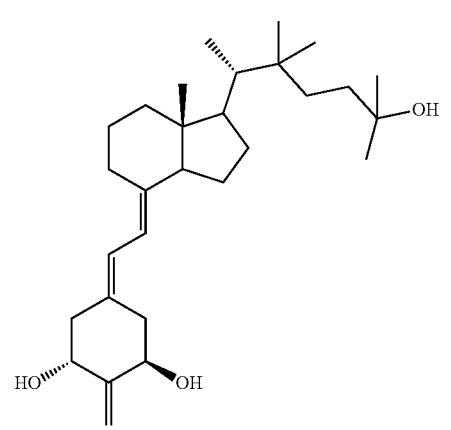

IIA

In some embodiments, the compound of formula IIA is a compound of formula IIC (MET-1), and in other embodiments, the compound of formula JIB is a compound of formula IID (MET-2) and have the structures shown below:

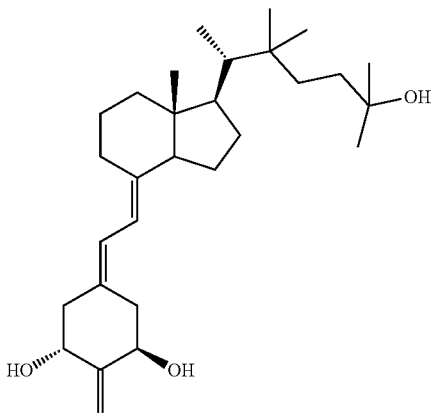

IIC

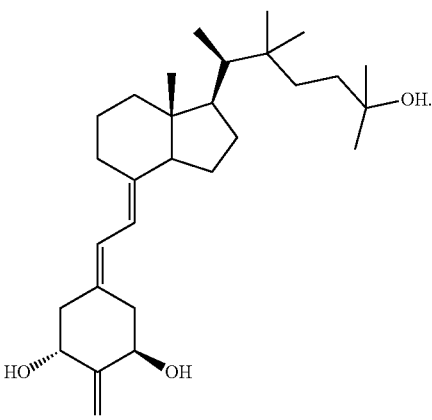

IID

Compounds of the present technology show a highly advantageous pattern of biological activity, including strong binding to the vitamin D receptor, strong cell differentiation and induction of 24-hydroxylase activity, yet low to very low calcemic activity. Thus the present compounds may be used in methods of treating a subject suffering from certain biological conditions. The methods include administering an effective amount of a compound of the present technology to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion.

A compound of the present technology may be present in a composition to treat the above-noted diseases and disorders in an effective amount and optionally including a pharmaceutically acceptable carrier. In some embodiments, the amount of compound includes from about 0.01 µg per gram of composition to about 1 mg per gram of the composition, preferably from about 0.1 µg per gram to about 500 µg per gram of the composition, and may be administered topically, transdermally, orally, or parenterally in dosages of from about 0.01 µg per day to about 1 mg per day, preferably from about 0.1 µg per day to about 500 µg per day.

Further features and advantages of the present technology will be apparent from the following detailed description and drawings.

BRIEF DESCRIPTION OF THE DRAWINGS

FIG. 1 shows a graph of competitive binding to the nuclear vitamin D hormone receptor between MET-1 and the native hormone, 1,25(OH)$_2$D$_3$. MET-1 binds to the nuclear vitamin D hormone receptor with the same affinity as 1,25(OH)$_2$D$_3$.

FIG. 2 is a graph comparing the percent HL-60 cell differentiation as a function of the concentration of MET-1 with that of 1,25(OH)$_2$D$_3$. MET-1 has the about four times the potency of 1,25(OH)$_2$D$_3$ in causing the differentiation of HL-60 cells into monocytes.

FIG. 3 is a graph comparing the in vitro transcription activity of MET-1 with that of 1,25(OH)$_2$D$_3$. MET-1 is about ten times more potent than 1,25(OH)$_2$D$_3$ in increasing transcription of the 24-hydroxylase gene.

FIG. 4 is a bar graph comparing the bone calcium mobilization activity of MET-1 with that of 1,25(OH)$_2$D$_3$ in rat. MET-1 is approximately 20 times less potent than 1,25(OH)$_2$D$_3$ in releasing bone calcium stores.

FIG. 5 is a bar graph comparing the intestinal calcium transport activity of MET-1 with that of 1,25(OH)$_2$D$_3$. MET-1 is less potent than 1,25(OH)$_2$D$_3$ in promoting active calcium transport in the rat gut.

FIG. 6 shows a graph of competitive binding to the nuclear vitamin D hormone receptor between MET-2 and the native hormone, 1,25(OH)$_2$D$_3$. MET-2 binds to the nuclear vitamin D hormone receptor with the same affinity as 1,25(OH)$_2$D$_3$.

FIG. 7 is a graph comparing the percent HL-60 cell differentiation as a function of the concentration of MET-2 with that of 1,25(OH)$_2$D$_3$. MET-2 has the about three times the potency of 1,25(OH)$_2$D$_3$ in causing the differentiation of HL-60 cells into monocytes.

FIG. 8 is a graph comparing the in vitro transcription activity of MET-2 with that of 1,25(OH)$_2$D$_3$. MET-2 is about three times more potent than 1,25(OH)$_2$D$_3$ in increasing transcription of the 24-hydroxylase gene.

FIG. 9 is a bar graph comparing the bone calcium mobilization activity of MET-2 with that of 1,25(OH)$_2$D$_3$ in rat. MET-2 is approximately 16 times less potent than 1,25(OH)$_2$D$_3$ in releasing bone calcium stores.

FIG. 10 is a bar graph comparing the intestinal calcium transport activity of MET-2 with that of 1,25(OH)$_2$D$_3$. MET-2 is less potent than 1,25(OH)$_2$D$_3$ in promoting active calcium transport in the rat gut.

Figure 1:
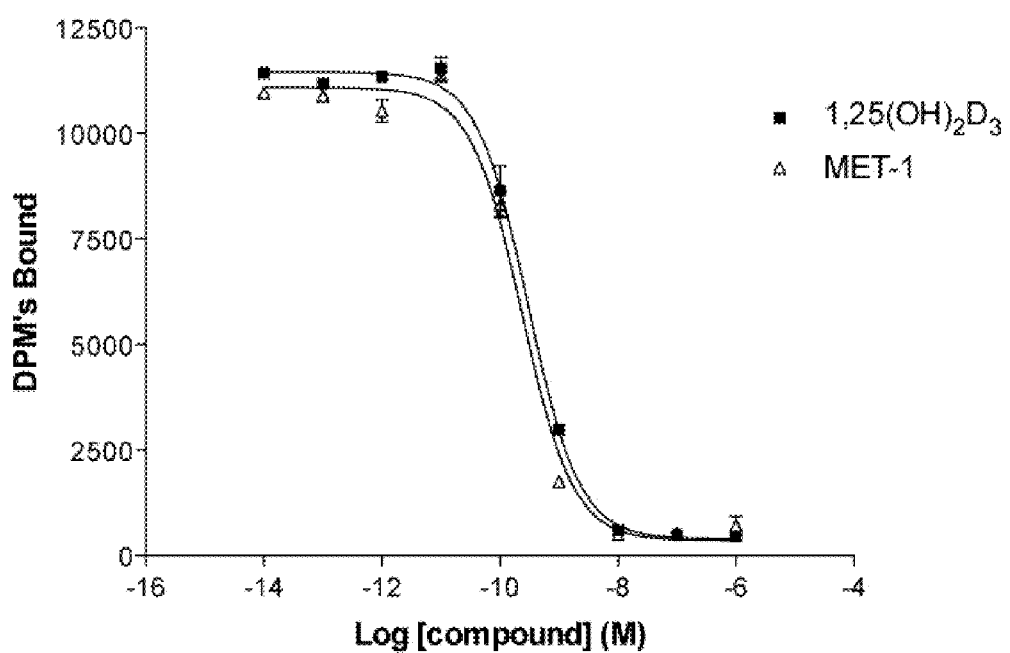
FIGS. 1-5 illustrate various biological activities of (20S)-2-methylene-19-nor-22-dimethyl-1α,25-dihydroxyvitamin $D_3$ (referred to as "MET-1" in the figures) compared with those of the native hormone 1α,25-dihydroxyvitamin $D_3$ (referred to as "1,25(OH)$_2$D$_3$" in the figures).

DETAILED DESCRIPTION (20S)-2-Methylene-19-nor-22-dimethyl-1α,25-dihydroxyvitamin $D_3$ and (20R)-2-methylene-19-nor-22-dimethyl-1α,25-dihydroxyvitamin $D_3$ were synthesized, and tested, and found to be useful in treating a variety of biological conditions as described herein. Structurally, these compounds have the formulas IIA and IIB as shown below:

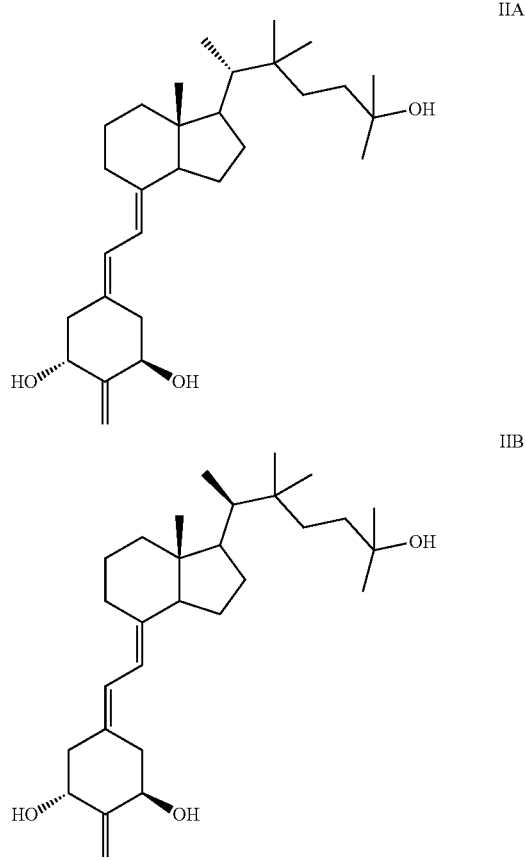

Preparation of (20S)-2-methylene-19-nor-22-dimethyl-1α,25-dihydroxyvitamin $D_3$ and (20R)-2-methylene-19-nor-22-dimethyl-1α,25-dihydroxyvitamin $D_3$ can be accomplished by condensing an appropriate bicyclic Windaus-Grundmann type ketone (IIIA or IIIB) with the allylic phosphine oxide IV followed by deprotection (removal of the Y, $Y_1$ and $Y_2$ hydroxy protecting groups).

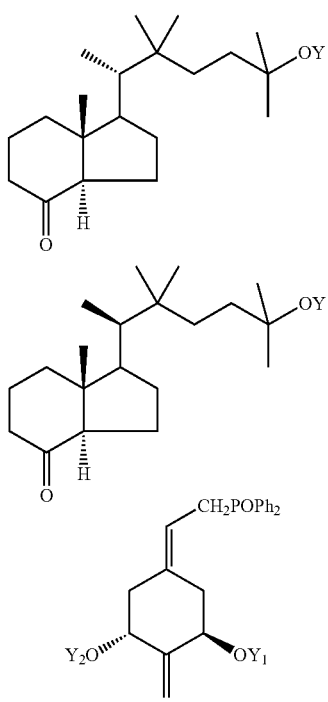

Hydraindanones of structure IIIA and IIIB can prepared by slight modification of known methods as will be readily apparent to one of skill in the art and described herein. Specific examples of methods used to synthesize bicyclic ketones for vitamin D analogs are those described in Mincione et al., *Synth. Commun* 19, 723, (1989); and Peterson et al., *J. Org. Chem.* 51, 1948, (1986). An overall process for synthesizing 2-alkylidene-19-nor-vitamin D compounds is illustrated and described in U.S. Pat. No. 5,843,928 which is hereby incorporated by reference in its entirety and for all purposes as if fully set forth herein. Details of preparing hydrinanones IIIA and IIIB are found in the Examples herein.

In phosphine oxide IV, $Y_1$ and $Y_2$ are hydroxy-protecting groups such as silyl protecting groups. The t-butyldimethylsilyl (TBDMS) group is an example of a particularly useful hydroxy-protecting group. The process described above represents an application of the convergent synthesis concept, which has been applied effectively to the preparation of numerous vitamin D compounds (see Lythgoe et al., *J. Chem. Soc. Perkin Trans. I*, 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

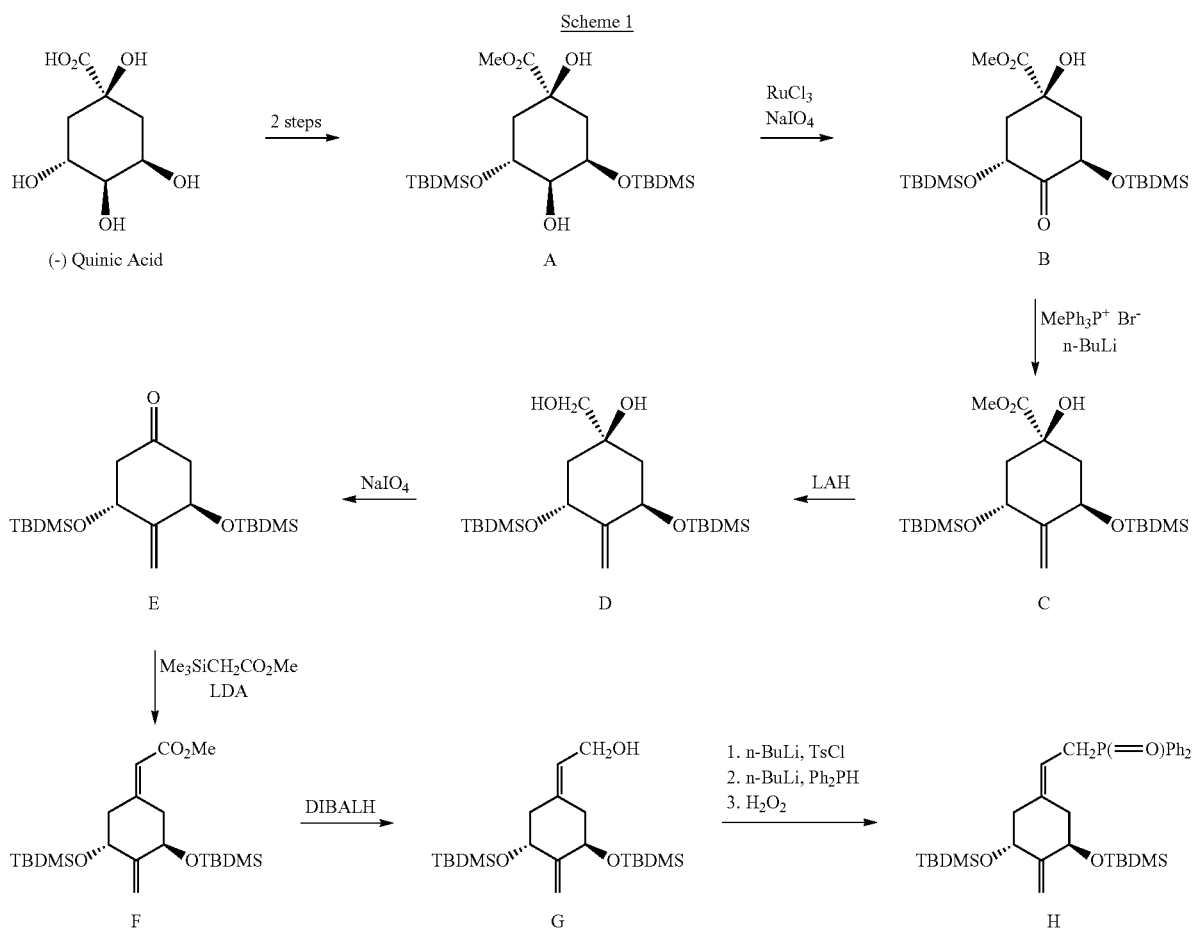

Scheme 1

Phosphine oxide IV is a convenient reagent that may be prepared according to the procedures described by Sicinski et al., *J. Med. Chem.*, 41, 4662 (1998), DeLuca et al., U.S. Pat. No. 5,843,928; Perlman et al., *Tetrahedron Lett.* 32, 7663 (1991); and DeLuca et al., U.S. Pat. No. 5,086,191. Scheme 1 shows the general procedure for synthesizing phosphine oxide IV as outlined in U.S. Pat. No. 5,843,928 which is hereby incorporated by reference in its entirety as if fully set forth herein.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groups such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

Figure 4:
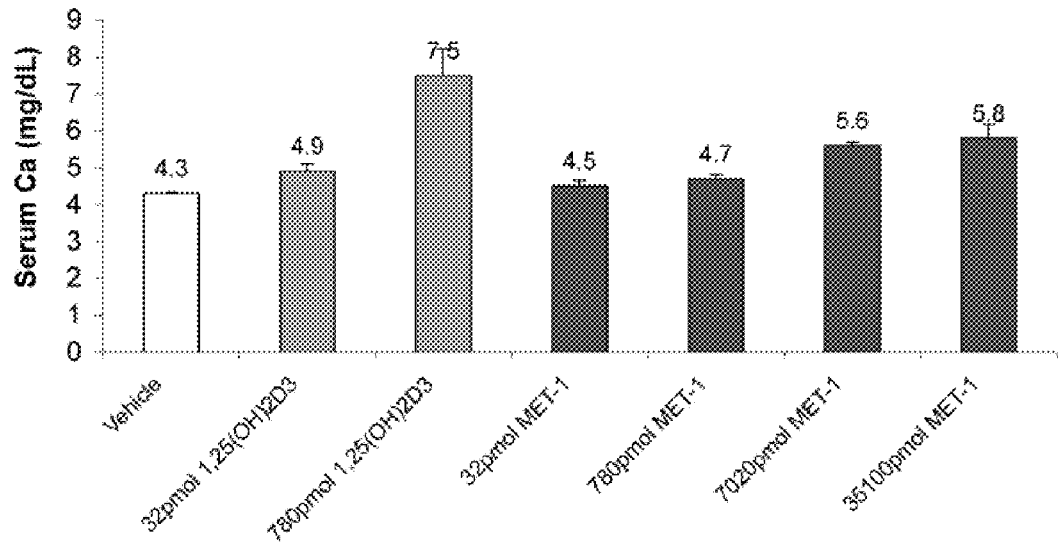
Figure 9:
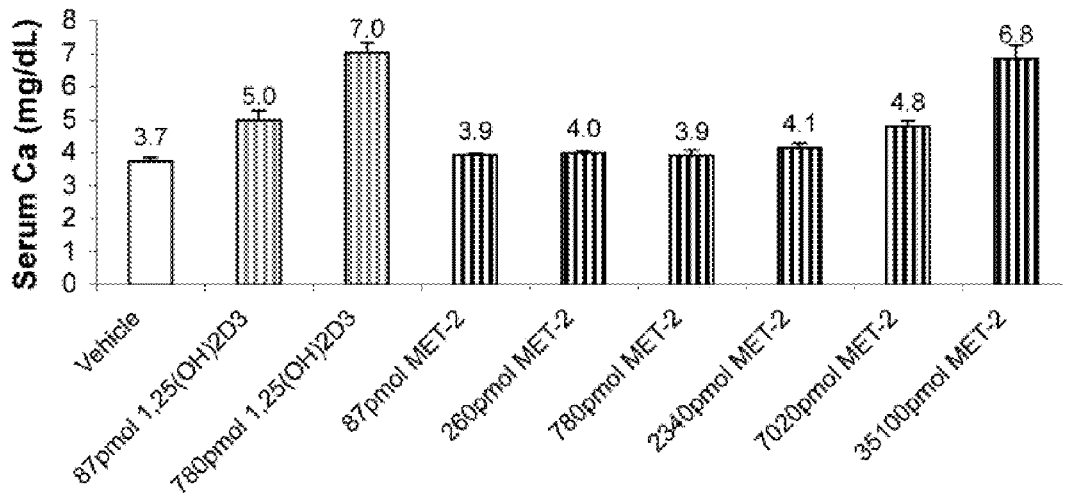
Figure 10:
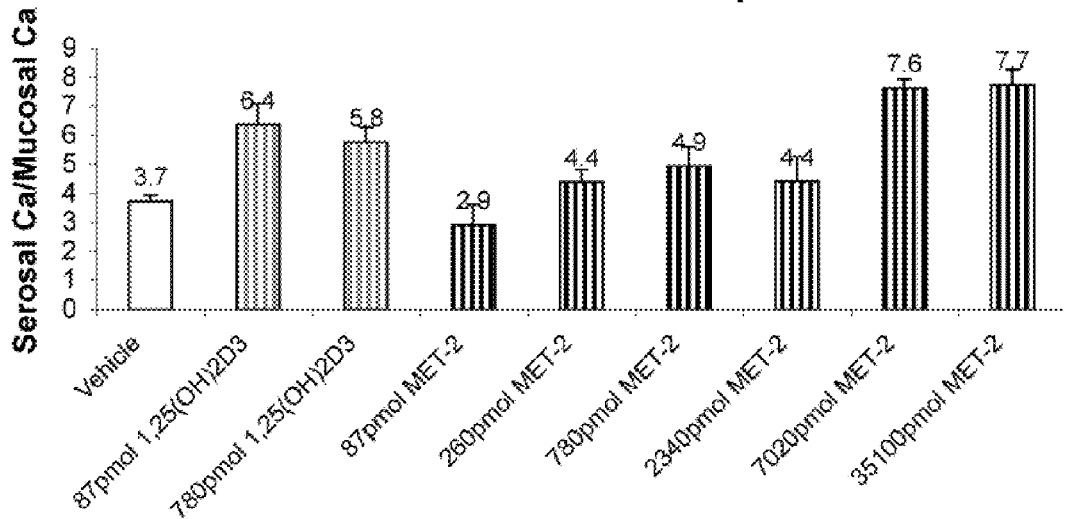

Compounds of the present technology exhibit desirable, and highly advantageous, patterns of biological activity. These compounds are characterized by relatively high binding to vitamin D receptors (see FIGS. 1 and 5) and high activity in HL-60 differentiation, but very low ability to mobilize calcium from bone (see FIGS. 4 and 9) and relatively low intestinal calcium transport activity (see FIGS. 5 and 10), as compared to that of 1α,25-dihydroxyvitamin $D_3$. Hence, these compounds can be characterized as having little, if any, calcemic activity at the dosages that 1α,25-dihydroxyvitamin $D_3$ displays significant calcemic activity. Thus, the may be useful as a therapy for suppression of secondary hyperparathyroidism type renal osteodystrophy.

The compounds of the present technology are also suited for treatment and prophylaxis of human disorders which are characterized by an imbalance in the immune system, e.g. in autoimmune diseases, including multiple sclerosis, lupus, diabetes mellitus, host versus graft reaction, and rejection of organ transplants; and additionally for the treatment of inflammatory diseases, such as rheumatoid arthritis, asthma, and inflammatory bowel diseases such as celiac disease, ulcerative colitis and Crohn's disease. Acne, alopecia and hypertension are other conditions which may be treated with the compounds of the present technology.

Figure 2:
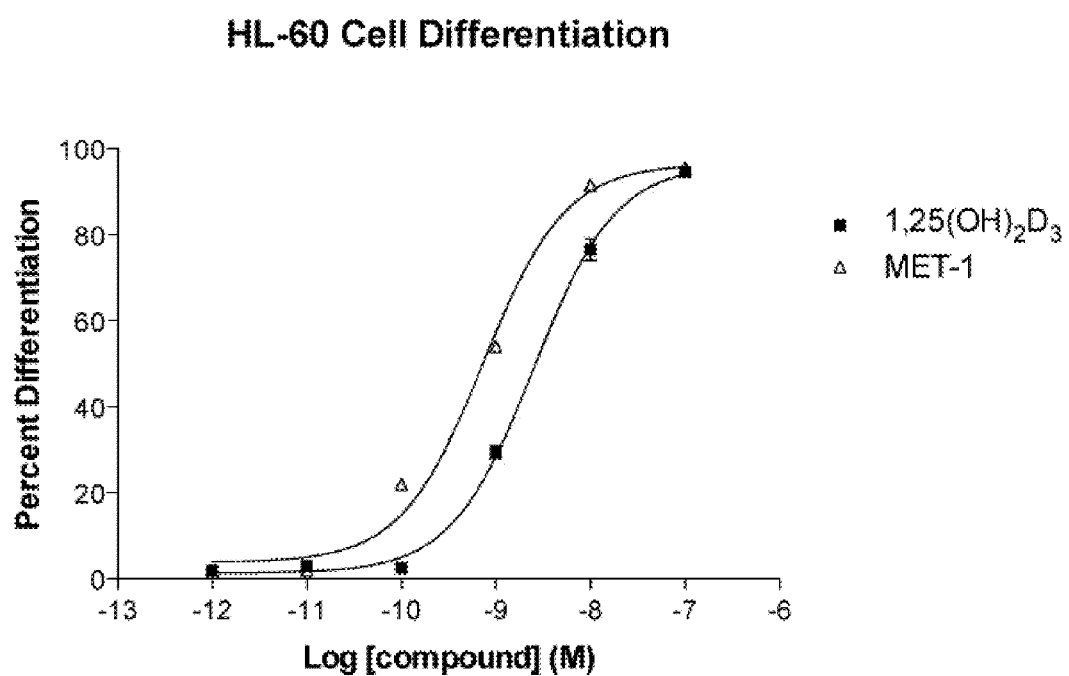
Figure 7:
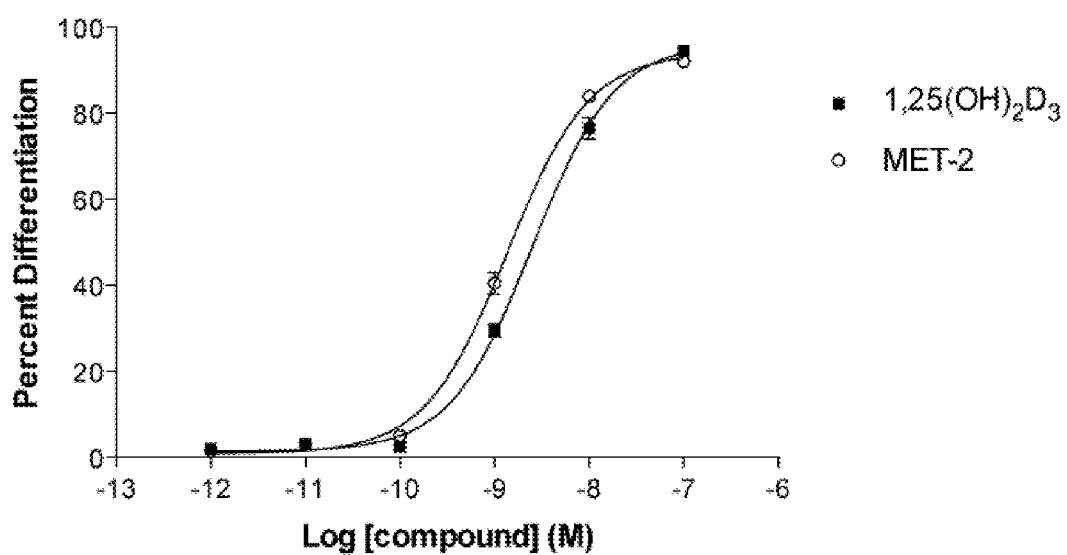

The above compounds are also characterized by cell differentiation activity either equal to or significantly higher than that of 1α,25(OH)$_2$ $D_3$ (see FIGS. 2 and 7). Thus, this compound also provides a therapeutic agent for the treatment of psoriasis, or as an anti-cancer agent, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin.

The compounds of the present technology may be used to prepare pharmaceutical formulations or medicaments that include a compound of the present technology in combination with a pharmaceutically acceptable carrier. Such pharmaceutical formulations and medicaments may be used to treat various biological disorders such as those described herein. Methods for treating such disorders typically include administering an effective amount of the compound or an appropriate amount of a pharmaceutical formulation or a medicament that includes the compound to a subject suffering from the biological disorder. In some embodiments, the subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the subject is a primate such as, in some embodiments, a human.

For treatment purposes, the compounds defined by formulas I, IA, IB, II, IIA, IIB, IIC, and IID may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the present technology. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from about 0.001 μg to about 1 mg per day of the compound are appropriate for treatment purposes. In some such embodiments an appropriate and effective dose may range from about 0.01 μg to about 1 mg per day of the compound. In other such embodiments an appropriate and effective dose may range from about 0.1 μg to about 500 μg per day of the compound. Such doses will be adjusted according to the type of disease or condition to be treated, the severity of the disease or condition, and the response of the subject as is well understood in the art. The compound may be suitably administered alone, or together with another active vitamin D compound.

Compositions for use in the present technology include an effective amount of (20S)-2-Methylene-19-nor-22-dimethyl-1α,25-dihydroxyvitamin $D_3$ and/or (20R)-2-methylene-19-nor-22-dimethyl-1α,25-dihydroxyvitamin $D_3$ as the active ingredient, and a suitable carrier. An effective amount of a compound herein for use in accordance with some embodiments of the present technology will generally be a dosage amount such as those described herein, and may be administered topically, transdermally, orally, nasally, rectally, or parenterally.

The compounds of formula IIA, IIB, IIC and IID may be advantageously administered in amounts sufficient to effect the differentiation of promyelocytes to normal macrophages. Dosages as described above are suitable, it being understood that the amounts given are to be adjusted in accordance with the severity of the disease, and the condition and response of the subject as is well understood in the art.

The compounds may be formulated as creams, lotions, ointments, aerosols, suppositories, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

The formulations of the present technology comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present technology suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

For nasal administration, inhalation of powder, self-propelling or spray formulations, dispensed with a spray can, a nebulizer or an atomizer can be used. The formulations, when dispensed, preferably have a particle size in the range of 10 to 100 microns.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

All references cited herein are specifically incorporated by reference in their entireties and for all purposes as if fully set forth herein.

EXAMPLES

Example 1

Synthesis of (20S)-2-methylene-19-nor-22-dimethyl-1α,25-dihydroxyvitamin $D_3$

Compounds of the present technology, including (20S)-2-methylene-19-nor-22-dimethyl-1α,25-dihydroxyvitamin $D_3$, were prepared using the methods shown in Schemes 1-3. As shown in Scheme 2, compound 2 is obtained by ozonolysis of vitamin $D_2$ (compound 1) as described by Sicinski et al. (*J. Med. Chem.* 41, 4662-4672, 1998), followed by reduction with borohydride. Treatment of the dialcohol 2 with tosyl chloride in pyridine provides the tosylate compound 3. Compound 3 is protected by treatment with triethylsilyl triflate (TESOTf) and 2,6-lutidine in dichloromethane to give compound 4. The tosylate of compound 4 was displaced with cyanide in dimethyl sulfoxide (DMSO) to give cyano compound 5. Reaction of compound 5 with lithium diisopropyl amide (LDA) in tetrahydrofuran (THF) and alkylation with methyl iodide provided compound 6, which was subsequently reduced with diisobutyl aluminum hydride (DIBAL) in dichloromethane to provide aldehyde 7.

Scheme 3 illustrates the conversion of compound 7 to the title compound of Formula IIA (compound 14). First, the aldehyde 7 is reacted with triethylphosphonoacetate 8 in the presence of LDA to provide alkene 9. Compound 9 was hydrogenated over Pd/C in methanol to give compound 10, and the latter compound was reacted with methyl Grignard reagent to give the tertiary alcohol, 11. Oxidation with tetrapropylperruthenate in the presence of N-methylmorpholine N-oxide, followed by protection of the remaining alcohol with TESOTf under the same conditions as before led to ketone 12. Compound 12 was coupled with the A-ring phosphonium salt (compound H from Scheme 1) using phenyl lithium to produce compound 13, the silyl protected vitamin derivative (a compound of formula I and IA). Removal of all the silyl protecting groups was effected with HF in acetonitrile (ACN) to give compound 14 (a compound of formula I and IIA). This product was fully characterized as described below.

Scheme 2
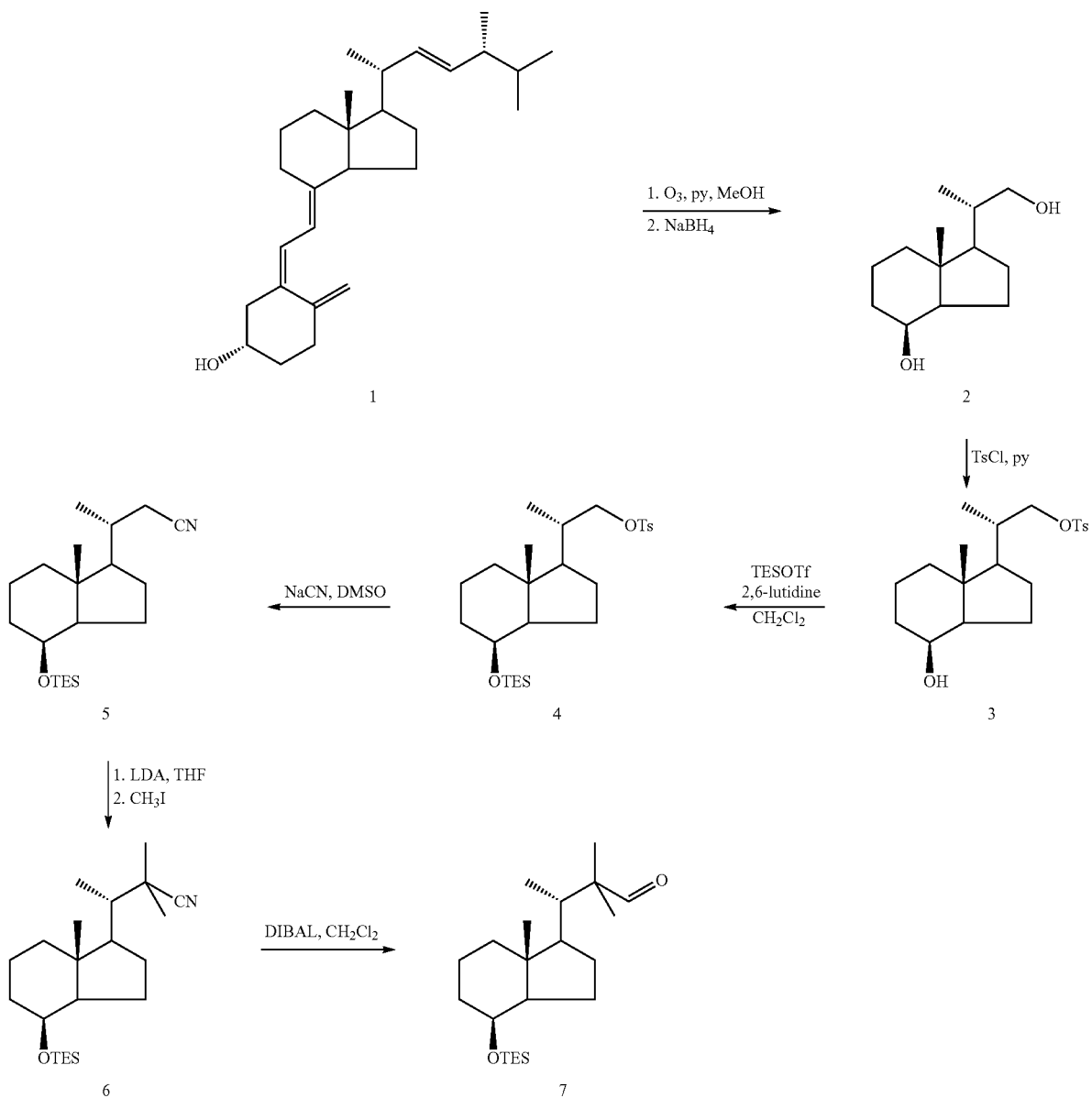
Scheme 3
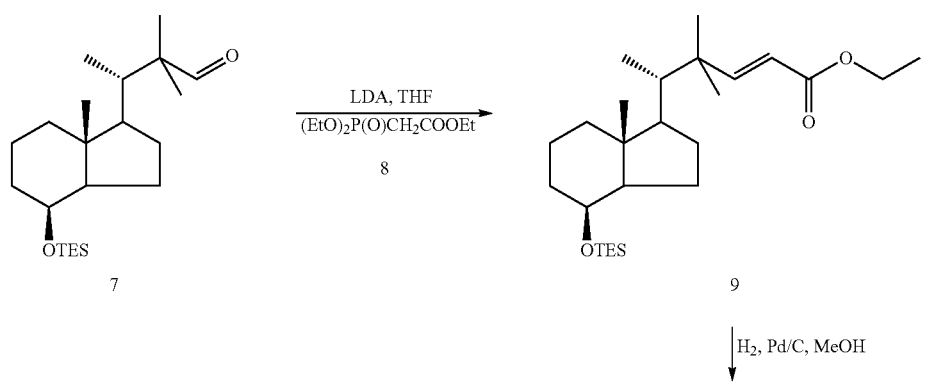

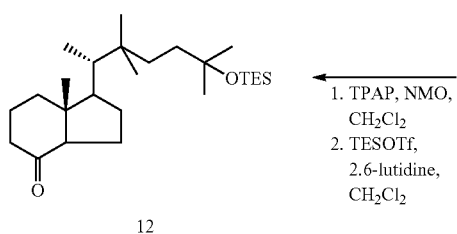

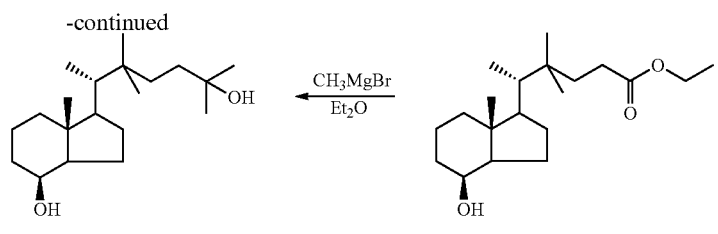

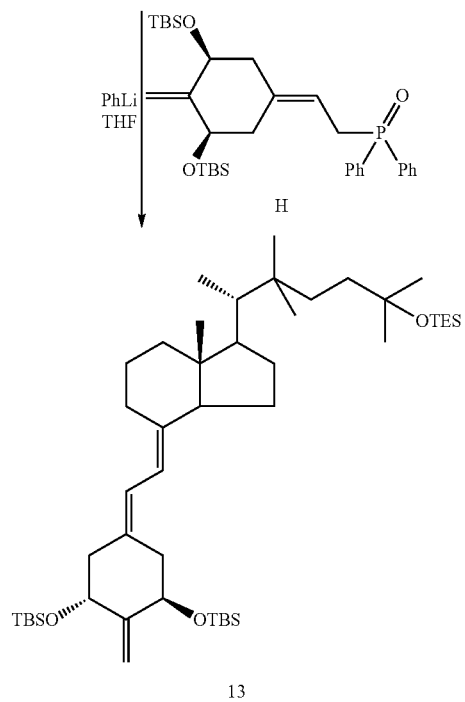

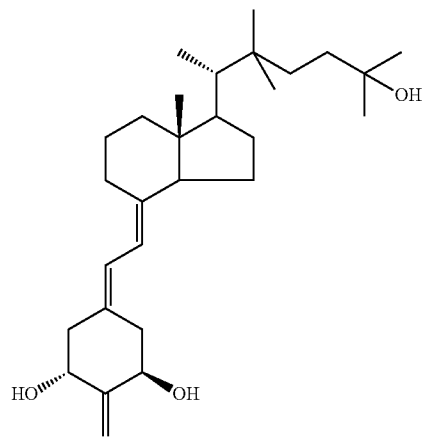

(8S,20S)-Des-A,B-20-(hydroxymethyl)-pregnan-8-ol (2)

Ozone was passed through a solution of vitamin D$_2$ 1 (5 g, 12.6 mmol) and pyridine (5 mL, 4.89 g, 62 mmol) in methanol (400 mL) at −78° C. When the reaction mixture turned deep blue it was flushed with oxygen for 15 min to remove the residual ozone and then it was treated with NaBH$_4$ (1.5 g, 40 mmol). After 15 min the second portion of NaBH$_4$ (1.5 g, 40 mmol) was added and the mixture was allowed to warm to room temperature. The third portion of NaBH$_4$ (1.5 g, 40 mmol) was added and the reaction mixture was stirred for 18 hours. The reaction was quenched with water, concentrated under reduced pressure and extracted with dichloromethane. The combined organic phases were washed with 1M aqueous HCl, saturated aqueous NaHCO$_3$ and dried (Na$_2$SO$_4$) and concentrated. The residue was purified by column chromatography on silica gel (30%, then 50% ethyl acetate/hexane) to give the diol 2 (2.61 g, 49%) as colorless crystals.

m.p. 107° C. (from ethyl acetate/hexane); [α]$_D$ +32.9 (c 1.0, CHCl$_3$); $^1$H NMR (500 MHz, CDCl$_3$) δ 4.07 (1H, d, J=2.5 Hz), 3.62 (1H, dd, J=10.5, 3.2 Hz), 3.37 (1H, dd, J=10.5, 6.8 Hz), 1.98 (1H, m), 1.80 (3H, m), 1.02 (3H, d, J=6.6 Hz), 0.94 (3H, s); $^{13}$C NMR (125 MHz, CDCl$_3$) δ 69.21, 67.81, 52.91, 52.34, 41.84, 40.20, 38.22, 33.55, 26.64, 22.55, 17.38, 16.60, 13.56; MS (EI) m/z 212 (1, M$^+$), 194 (28, M$^+$−H$_2$O), 179 (29), 163 (22), 147 (15), 135 (42), 125 (48), 111 (100), 97 (51); exact mass calculated for C$_{13}$H$_{22}$O (M$^+$−H$_2$O) 194.1671, found 194.1673.

(8S,20S)-Des-A,B-20-[(p-toluenesulfonyl)oxy]methyl-pregnan-8-ol (3)

A precooled (−20° C.) solution of tosyl chloride (0.9 g, 4.73 mmol) in pyridine (2 mL) was added to a mixture of the diol 2 (0.52 g, 2.45 mmol) in dry pyridine (5 mL) at −20° C. The reaction mixture was stirred for 3 h at −20° C., then it was warmed to 0° C. and stirred for 18 h. The mixture was pulled into a saturated aqueous CuSO$_4$ solution and extracted with dichloromethane. Combined organic phases were washed with a saturated aqueous CuSO$_4$ solution and dried (Na$_2$SO$_4$) and concentrated. The residue was purified by column chromatography on silica gel (20% ethyl acetate/hexane) to afford of tosylate 3 (0.86 g, 96% yield) as colorless crystals.

m.p. 95° C. (from ethyl acetate/hexane); [α]$_D$ +17.4 (c 1.0, CHCl$_3$); $^1$H NMR (400 MHz, CDCl$_3$) δ 7.77 (2H, d, J=8.2 Hz), 7.34 (2H, d, J=8.2 Hz), 4.06 (1H, s), 3.94 (1H, dd, J=9.2, 3.1 Hz), 3.80 (1H, dd, J=9.2, 6.2 Hz), 2.44 (3H, s), 1.90 (1H, m), 1.78 (2H, m), 0.95 (3H, d, J=6.6 Hz), 0.88 (3H, s); $^{13}$C NMR (100 MHz, CDCl$_3$) δ 144.59, 133.01, 129.73, 127.86, 75.56, 68.98, 52.18, 41.81, 40.00, 35.66, 33.50, 26.36, 22.40, 21.60, 17.29, 16.69, 13.43; MS (EI) m/z 367 (6, MH$^+$), 348

(5, M$^+$–H$_2$O), 307 (2), 194 (18), 179 (23), 150 (17), 135 (16), 125 (34), 111 (100), 91 (50); MS (ESI) m/z 389 (100, [M+Na]$^+$), 755 (90, [2M+Na]$^+$), 1121 (60, [3M+Na]$^+$); exact mass (ESI) calculated for C$_{20}$H$_{30}$O$_4$SNa [M+Na]$^+$ 389.1763, found 389.1758.

(8S,20S)-Des-A,B-8-[(triethylsilyl)oxy]-20-[(p-toluenesulfonyl)oxy]methyl-pregnane (4)

Triethylsilyl trifluoromethanesulfonate (0.6 mL, 0.70 g, 2.65 mmol) was added to a solution of the tosylate 3 (0.65 g; 1.78 mmol) and 2,6-lutidine (0.3 mL, 0.28 g, 2.58 mmol) in dichloromethane (6 mL) at 0° C. The reaction mixture was stirred for 15 min and it was diluted with dichloromethane. The organic phase was washed with water, dried (Na$_2$SO$_4$) and concentrated. The residue was purified by column chromatography on silica gel (20% ethyl acetate/hexane) to give the product 4 (0.84 g, 99% yield) as a light yellow oil.

[α]$_D$ +20.6 (c 1.0, CHCl$_3$); $^1$H NMR (400 MHz, CDCl$_3$) δ 7.78 (2H, d, J=8.2 Hz), 7.34 (2H, d, J=8.2 Hz), 4.01 (1H, d, J=2.0 Hz), 3.96 (1H, dd, J=9.2, 3.0 Hz), 3.79 (1H, dd, J=9.2, 6.5 Hz), 2.45 (3H, s), 1.87 (1H, m), 0.94 (3H, d, J=5.9 Hz), 0.93 (9H, t, J=7.9 Hz), 0.86 (3H, s), 0.54 (6H, q, J=7.9 Hz); $^{13}$C NMR (125 MHz, CDCl$_3$) δ 144.55 (0), 133.10 (0), 129.73 (1), 127.91 (1), 75.76 (2), 69.11 (1), 52.70 (1), 52.36 (1), 42.12 (0), 40.39 (2), 35.72 (1), 34.47 (2), 26.52 (2), 22.88 (2), 21.63 (3), 17.56 (2), 16.76 (3), 13.46 (3), 6.91 (3), 4.89 (2); MS (EI) m/z no M$^+$, 319 (46), 291 (9), 265 (9), 246 (5), 217 (100), 189 (81), 161 (69), 133 (54), 103 (38), 94 (39); MS (ESI) m/z 503 (100, [M+Na]$^+$), 983 (40, [2M+Na]$^+$), 1463 (71, [3M+Na]$^+$); exact mass (ESI) calculated for C$_{26}$H$_{44}$O$_4$SSiNa [M+Na]$^+$ 503.2627, found 503.2629.

(8S,20R)-Des-A,B-8-[(triethylsilyl)oxy]-20-(cyanomethyl)-pregnane (5)

Sodium cyanide (2 g, 41 mmol) was added to a solution of tosylate 4 (0.84 g, 1.75 mmol) in dry DMSO (8 mL). The resulting mixture was stirred at 90° C. for 3 h, then it was cooled, diluted with water and extracted with ethyl acetate. Combined organic phases were dried (Na$_2$SO$_4$) and concentrated. The residue was purified by column chromatography on silica gel (10% ethyl acetate/hexane) to give the cyanide 5 (0.57 g, 97% yield) as a colorless oil.

[α]$_D$ +16.6 (c 1.0, CHCl$_3$); $^1$H NMR (400 MHz, CDCl$_3$) δ 4.04 (1H, d, J=2.1 Hz), 2.34 (1H, dd, J=16.6, 3.7 Hz), 2.23 (1H, dd, J=16.6, 7.0 Hz), 1.92 (1H, m), 1.13 (3H, d, J=6.6 Hz), 0.942 (9H, t, J=7.9 Hz), 0.921 (3H, s), 0.55 (6H, q, J=7.9 Hz); $^{13}$C NMR (125 MHz, CDCl$_3$) δ 119.09 (0), 69.12 (1), 55.34 (1), 52.86 (1), 42.18 (0), 40.35 (2), 34.40 (2), 33.09 (1), 27.19 (2), 24.69 (2), 22.82 (2), 19.23 (3), 17.53 (2), 13.63 (3), 6.91 (3), 4.89 (2); MS (EI) m/z 335 (10), 320 (3), 306 (100), 292 (28), 225 (7), 202 (20), 188 (10), 161 (17), 135 (14), 103 (55); exact mass calculated for C$_{20}$H$_{37}$ONSi (M$^+$) 335.2644, found 335.2656.

(8S,20S)-Des-A,B-8-[(triethylsilyl)oxy]-20-(1'-methyl-1'-cyano-ethyl)-pregnane (6)

n-Butyllithium (1.6 M in hexane, 3.4 mL, 5.4 mmol) was added to a solution of diisopropylamine (0.76 mL, 0.544 g, 5.4 mmol) in THF (1 mL) at 0° C. The resulting mixture was stirred at 0° C. for 30 min, then it was cooled to –78° C. and a solution of cyanide 5 (0.45 g, 1.34 mmol) in THF (2 mL) was added. The mixture was stirred at –78° C. for 30 min and then iodomethane (0.9 mL, 2.04 g, 14.4 mmol) was added. The reaction mixture was stirred at –78° C. for 1 h and then at room temperature for 1 h. It was quenched with saturated aqueous NH$_4$Cl solution and extracted with ethyl acetate. Combined organic phases were washed with brine, dried (Na$_2$SO$_4$) and concentrated. The residue was purified by column chromatography on silica gel (10%, then 20% ethyl acetate/hexane) to give the product 6 (0.49 g, 100% yield).

[α]$_D$ +34.5 (c 1.0, CHCl$_3$); $^1$H NMR (400 MHz, CDCl$_3$) δ 4.04 (1H, d, J=2.5 Hz), 1.37 (3H, s), 1.28 (3H, s), 0.99 (3H, d, J=6.9 Hz), 0.97 (3H, s), 0.95 (9H, t, J=7.9 Hz), 0.55 (6H, q, J=7.9 Hz); $^{13}$C NMR (100 MHz, CDCl$_3$) δ 127.28 (0), 69.26 (1), 54.06 (1), 52.33 (1), 43.55 (0), 42.77 (1), 41.17 (2), 35.67 (0), 34.48 (2), 27.97 (2), 27.43 (3), 23.45 (2), 22.70 (3), 17.69 (2), 14.60 (3), 13.17 (3), 6.92 (3), 4.91 (2); MS (EI) m/z 363 (28, M$^+$), 349 (14), 334 (100), 321 (65), 306 (27), 261 (11), 225 (27), 183 (14), 163 (36), 135 (47), 103 (99), 75 (58); exact mass calculated for C$_{22}$H$_{41}$ONSi (M$^+$) 363.2957, found 363.2957.

(8S,20S)-Des-A,B-8-[(triethylsilyl)oxy]-20-(1'-methyl-1'-formyl-ethyl)-pregnane (7)

Diisobutylaluminium hydride (1.0 M in dichloromethane, 2.5 mL, 2.5 mmol) was added to a solution of the compound 6 (0.49 g, 1.35 mmol) in dichloromethane (3 mL) at –10° C. The reaction mixture was stirred at –10° C. for 1 hour, then it was quenched with a saturated aqueous sodium potassium tartrate solution (5 mL). The water phase was extracted with dichloromethane. Combined organic layers were washed with brine and dried (Na$_2$SO$_4$) and concentrated. The residue was purified by column chromatography on silica gel (10%, then 20% ethyl acetate/hexane) to give the aldehyde 7 (0.47 g, 95% yield) as colorless crystals. m.p. 71-72° C. (EtOAc); [α]$_D$ +12.8 (c 1.0, CHCl$_3$); $^1$H NMR (400 MHz, CDCl$_3$) δ 9.48 (1H, s), 4.00 (1H, d, J=2.2 Hz), 2.00 (1H, m), 0.95 (6H, s), 0.94 (9H, t, J=7.8 Hz), 0.94 (3H, d, J=6.9 Hz), 0.93 (3H, s), 0.54 (6H, q, J=7.8 Hz); $^{13}$C NMR (100 MHz, CDCl$_3$) δ 207.03 (1), 69.30 (1), 54.46 (1), 52.65 (1), 50.05 (0), 43.02 (0), 41.22 (2), 40.21 (1), 34.57 (2), 28.73 (2), 23.34 (2), 22.74 (3), 17.72 (2), 15.20 (3), 13.61 (3), 13.22 (3), 6.92 (3), 4.92 (2); MS (EI) m/z 366 (3, M$^+$), 337 (10), 323 (4), 295 (10), 281 (5), 253 (6), 239 (8), 225 (38), 203 (6), 186 (22), 163 (100), 135 (56), 103 (87), 75 (63); exact mass (ESI) calculated for C$_{22}$H$_{42}$O$_2$SiNa [M+Na]$^+$ 389.2852, found 389.2855.

(8S,20S)-Des-A,B-8-[(triethylsilyl)oxy]-20-(1'-dimethyl-3'-ethyloxycarbonyl-2'-propenyl)-pregnane (9)

n-Butyllithium (1.6 M in hexane, 1.1 mL, 1.76 mmol) was added to a solution of diisopropylamine (0.24 mL, 0.172 g, 1.70 mmol) in dry THF (1 mL) at 0° C. After 30 min the mixture was cooled to –10° C. and triethylphosphonoacetate 8 (0.38 mL, 0.426 g, 1.9 mmol) was added. The reaction mixture was stirred at –10° C. for 30 min and then a solution of aldehyde 7 (31.4 mg, 0.086 mmol) in anhydrous THF (1 mL+0.5 mL) was added via cannula. The mixture was stirred under argon at –10° C. for 1 h, then it was heated to 37° C. for 2.5 h and later it was stirred at room temperature overnight. Dichloromethane was added and the organic phase was washed with water, dried (Na$_2$SO$_4$) and concentrated. The product was purified on Sep-Pak cartridge (5 g). The cartridge was washed with hexane/ethyl acetate (2%) to give 9 (34.1 mg, 91% yield) as a colorless oil. [α]$_D$ –4.6 (c 1.0, CHCl$_3$); $^1$H NMR (400 MHz, CDCl$_3$) δ 7.07 (1H, d, J=16.0 Hz), 5.64 (1H, d, J=16.0 Hz), 4.19 (2H, q, J=7.1 Hz), 4.00 (1H, d, J=2.1 Hz), 2.00 (1H, m), 1.30 (3H, t, J=7.1 Hz), 1.00 (3H, s), 0.98 (3H, s), 0.94 (9H, t, J=7.9 Hz), 0.93 (3H, s), 0.93 (3H, d, J=8.0 Hz), 0.54 (6H, q, J=7.9 Hz); $^{13}$C NMR (100 MHz, CDCl$_3$) δ

167.52 (0), 162.38 (1), 115.17 (1), 69.44 (1), 60.04 (2), 54.44 (1), 52.45 (1), 45.28 (1), 43.45 (0), 41.30 (2), 40.91 (0), 34.59 (2), 29.75 (2), 27.44 (3), 23.79 (2), 21.34 (3), 17.74 (2), 15.03 (3), 14.29 (3), 13.01 (3), 6.92 (3), 4.92 (2); MS (EI) m/z 437 (4, MH$^+$), 421 (4), 407 (43), 366 (5), 337 (5), 295 (42), 281 (13), 256 (42), 225 (18), 191 (27), 163 (100); MS (ESI) m/z 459 (81, [M+Na]$^+$), 895 (75, [2M+Na]$^+$), 1331 (94, [3M+Na]$^+$), exact mass (ESI) calculated for $C_{26}H_{48}O_3SiNa$ [M+Na]$^+$ 459.3270, found 459.3254.

(8S,20S)-Des-A,B-20-(1'-dimethyl-3'-ethyloxycarbonyl-propyl)-pregnan-8-ol (10)

A solution of the ester 9 (34.1 mg, 0.078 mmol) in methanol (5 mL) was hydrogenated in the presence of 10% palladium on powdered charcoal (10 mg) at room temperature for 20 h. The reaction mixture was filtered through a Waters silica Sep-Pak cartridge (2 g), which was further washed with methanol. After removal of the solvent the ester 10 (24.0 mg, 95%) was obtained as a colorless oil. $[\alpha]_D$ +7.1 (c 1.0, CHCl$_3$); $^1$H NMR (500 MHz, CDCl$_3$) δ 4.12 (2H, q, J=7.1 Hz), 4.07 (1H, d, J=2.1 Hz), 2.25 (2H, m), 2.10 (1H, m), 1.26 (3H, t, J=7.1 Hz), 0.99 (3H, s), 0.92 (3H, d, J=7.1 Hz), 0.91 (3H, s), 0.86 (3H, s); $^{13}$C NMR (125 MHz, CDCl$_3$) δ 174.60 (0), 69.47 (1), 60.23 (2), 53.30 (1), 51.90 (1), 43.53 (0), 43.14 (1), 40.90 (2), 36.34 (0), 36.25 (2), 33.57 (2), 29.94 (2), 29.44 (2), 27.49 (3), 26.21 (3), 23.36 (2), 17.48 (2), 14.89 (3), 14.22 (3), 13.08 (3); MS (EI) m/z 325 (3, MH$^+$), 306 (5), 278 (8), 261 (7), 224 (7), 181 (15), 163 (56), 143 (100), 111 (76), 97 (62); MS (ESI) m/z 347 (85, [M+Na]$^+$), 671 (9, [2M+Na]$^+$), exact mass calculated for na$C_{20}H_{36}O_3$Na [M+Na]$^+$ 347.2562, found 347.2556.

(8S,20S)-Des-A,B-22-dimethyl-cholestan-8,25-diol (11)

Methylmagnesium bromide (3.0 M solution in diethyl ether, 65 μL, 0.195 mmol) was added to a solution of the ester 10 (24 mg, 0.074 mmol) in anhydrous diethyl ether (1.8 mL) at 0° C. The reaction mixture was stirred at 0° C. for 2 h and then at room temperature for 18 h. It was quenched with saturated aqueous NH$_4$Cl solution, extracted with ethyl acetate, dried (Na$_2$SO$_4$) and concentrated. The residue was applied to a Waters silica Sep-Pak cartridge (5 g). Elution with ethyl acetete/hexane (1:1) gave the diol 11 (19.2 mg, 84%). $[\alpha]_D$ +4.8 (c 1.0, CHCl$_3$); $^1$H NMR (400 MHz, CDCl$_3$) δ 4.07 (1H, d, J=2.1 Hz), 2.10 (1H, m), 1.21 (6H, s), 0.99 (3H, s), 0.91 (3H, s), 0.90 (3H, d, J=8.2 Hz), 0.84 (3H, s); $^{13}$C NMR (100 MHz, CDCl$_3$) δ 71.19 (0), 69.51 (1), 53.43 (1), 51.91 (1), 43.51 (0), 42.65 (1), 40.91 (2), 37.59 (2), 36.29 (2), 36.24 (0), 33.55 (2), 29.89 (2), 29.23 (3), 29.17 (3), 28.04 (3), 26.29 (3), 23.38 (2), 17.49 (2), 14.87 (3), 13.10 (3); MS (EI) m/z no M$^+$, 292 (5), 259 (2), 223 (3), 205 (7), 181 (8), 163 (28), 129 (25), 111 (100), 95 (23); MS (ESI) m/z 333 (95, [M+Na]$^+$), 643 (11, [2M+Na]$^+$), exact mass (ESI) calculated for na$C_{20}H_{38}O_2$Na [M+Na]$^+$ 333.2770, found 333.2774.

(20S)-Des-A,B-22-dimethyl-25-[(triethylsilyl)oxy]-cholestan-8-one (12)

Molecular sieves A4 (100 mg) were added to a solution of 4-methylmorpholine oxide (150 mg, 1.28 mmol) in dichloromethane (600 μL). The mixture was stirred at room temperature for 15 min and tetrapropylammonium perruthenate (8 mg, 22.8 μmol) was added, followed by a solution of diol 11 (19 mg, 0.061 mmol) in dichloromethane (400+200 μL). The resulting suspension was stirred at room temperature for 1 h. The reaction mixture was filtered through a Waters silica Sep-Pak cartridge (2 g) that was further washed with ethyl acetate. After removal of the solvent the ketone (19 mg) was obtained as a colorless oil.

Triethylsilyl trifluoromethanesulfonate (20 μL, 23 mg, 0.088 mmol) was added dropwise to a solution of the ketone (19 mg, 0.062 mmol) and 2,6-lutidine (60 μL, 55 mg, 0.515 mmol) in dichloromethane (1.2 mL) at −40° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (5 g). Elution with hexane/ethyl acetate (1%, then 2%) gave the protected ketone 12 (20.2 mg, 78% yield).

$[\alpha]_D$ −19.2 (c 1.0, CHCl$_3$); $^1$H NMR (400 MHz, CDCl$_3$) δ 2.33 (1H, d, J=11.5, 7.5 Hz), 2.24 (3H, m), 1.19 (6H, s), 0.95 (9H, t, J=7.9 Hz), 0.95 (3H, d, J=6.9 Hz), 0.89 (3H, s), 0.84 (3H, s), 0.71 (3H, s), 0.56 (6H, q, J=7.9 Hz); $^{13}$C NMR (100 MHz, CDCl$_3$) δ 212.46 (0), 73.40 (0), 61.73 (1), 53.18 (1), 51.09 (0), 43.36 (1), 41.08 (2), 39.48 (2), 38.77 (2), 36.15 (0), 35.76 (2), 30.76 (2), 29.87 (3), 27.70 (3), 26.24 (3), 23.94 (2), 19.96 (2), 14.72 (3), 12.87 (3), 7.14 (3), 6.81 (2); MS (EI) m/z no M$^+$, 407 (10), 393 (28), 364 (11), 294 (12), 273 (10), 173 (48), 163 (28), 111 (100); MS (ESI) m/z 445 (8, [M+Na]$^+$ exact mass (ESI) calculated for $C_{26}H_{50}O_2SiNa$ [M+Na]$^+$ 445.3478, found 445.3486.

20S-2-Methylene-19-nor-22-dimethyl-1α,25-dihydroxyvitamin D$_3$ (14)

Phenyllithium (1.83 M in di-n-butylether, 0.1 mL, 0.183 mmol) was added to a stirred solution of the phosphine oxide H (110 mg, 0.189 mmol) in anhydrous THF (1 mL) at −30° C. After 30 min the mixture was cooled to −78° C. and a precooled solution of the ketone 12 (20 mg, 47.4 μmol) in anhydrous THF (200+100 μL) was added. The reaction mixture was stirred under argon at −78° C. for 4 hours and then at +4° C. for 19 h. Ethyl acetate was added and the organic phase was washed with brine, dried (Na$_2$SO$_4$) and concentrated. The residue was applied to a Waters silica Sep-Pak cartridge (5 g). The cartridge was washed with hexane and ethyl acetate/hexane (1:99) to give the crude product. The vitamin was further purified by straight phase HPLC [9.4×250 mm Zorbax Silica column, 4 mL/min, hexane/2-propanol (0.1%) solvent system, R$_f$=3.4 min.] to give the pure protected compound 13 (33.83 mg, 91% yield).

UV (in hexane) $\lambda_{max}$ 263.5, 253.5, 245.5 nm; $^1$H NMR (400 MHz, CDCl$_3$) δ 6.22 (1H, d, J=11.1 Hz, 6-H), 5.85 (1H, d, J=11.1 Hz, 7-H), 4.97 (1H, s, =CH$_2$), 4.92 (1H, s, =CH$_2$), 4.43 (2H, m, 1β-H and 3α-H), 2.81 (1H, dm, J=12.6 Hz), 2.52 (1H, dd, J=13.3, 5.9 Hz, 10α-H), 2.47 (1H, dd, J=12.6, 4.5 Hz, 4α-H), 2.34 (1H, dd, J=13.3, 2.8 Hz, 10β-H), 2.18 (1H, dd, J=12.6, 8.3 Hz, 4β-H), 2.09 (1H, m), 1.97 (2H, m), 1.19 (6H, bs, 26-H$_3$, 27-H$_3$), 0.95 (9H, t, J=7.9 Hz), 0.93 (3H, d, J=6.8 Hz, 21-H$_3$), 0.897 (9H, s, t-BuSi), 0.868 (9H, s, t-BuSi), 0.889 and 0.833 (each 3H, each s, 28-H$_3$, 30-H$_3$), 0.62 (3H, s, 18-H$_3$), 0.57 (6H, q, J=7.9 Hz), 0.080 (3H, s, SiMe), 0.068 (3H, s, SiMe), 0.049 (3H, s, SiMe), 0.027 (3H, s, SiMe); $^{13}$C NMR (100 MHz, CDCl$_3$) δ 152.98 (0, C-2), 141.40 (0, C-8), 132.77 (0, C-5), 122.46 (1, C-6), 116.43 (1, C-7), 106.25 (2, =CH$_2$), 73.52 (0, C-25), 72.53 and 71.64 (each 1, C-1, C-3), 56.02 (1), 52.84 (1), 47.60 (2), 46.96 (0, C-13), 44.18 (1), 41.14 (2), 38.84 (2), 38.57 (2), 36.23 (0, C-22), 35.85 (2), 31.28 (2), 29.91 and 29.86 (each 3, C-26, C-27), 28.84 (2), 27.75 (3), 26.22 (3), 25.84 (3), 25.78 (3), 23.53 (2), 23.17 (2), 18.25 (0), 18.17 (0), 14.70 (3), 12.53 (3), 7.15 (3), 6.84 (2), −4.86 (3), −5.10 (3); MS (ESI) m/z 809 (2, [M+Na]$^+$), exact mass (ESI) calculated for $C_{47}H_{90}O_3Si_3Na$ [M+Na]$^+$ 809.6096, found 809.6086.

The protected compound 13 (33.82 mg, 43.0 mol) was dissolved in THF (4 mL) and acetonitrile (3 mL). A solution of aqueous 48% HF in acetonitrile (1:9 ratio, 4 mL) was added at 0° C. and the resulting mixture was stirred at room temperature for 3 h. Saturated aqueous NaHCO$_3$ solution was added and the reaction mixture was extracted with dichloromethane. The combined organic phases were dried (Na$_2$SO$_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product 14. The vitamin 14 was further purified by straight phase HPLC [9.4×250 mm Zorbax Silica column, 4 mL/min, hexane/2-propanol (85:15) solvent system, $R_f$=7.8 min.] and reverse phase HPLC [9.4×250 mm Zorbax RX-C18 column, 3 mL/min, methanol/water (85:15) solvent system, $R_f$=15.7 min.] to give the pure compound 14 (14.336 mg, 75% yield).

UV (in EtOH) $\lambda_{max}$ 261.5, 252.0, 244.5 nm; $^1$H NMR (500 MHz, CDCl$_3$) δ 6.35 (1H, d, J=11.2 Hz, 6-H), 5.89 (1H, d, J=11.2 Hz, 7-H), 5.10 (1H, s, =CH$_2$), 5.08 (1H, s, =CH$_2$), 4.48 (2H, m, 1β-H and 3α-H), 2.84 (1H, dd, J=13.0, 4.3 Hz, 10β-H), 2.80 (1H, dd, J=13.3, 4.1 Hz, 9β-H), 2.56 (1H, dd, J=13.4, 3.3 Hz, 4α-H), 2.32 (1H, dd, J=13.4, 6.1 Hz, 4β-H), 2.28 (1H, dd, J=13.0 Hz, 8.4 Hz, 10α-H), 2.08 (1H, m), 1.21 (6H, s, 26-H$_3$, 27-H$_3$), 0.92 (3H, d, J=7.0 Hz, 21-H$_3$), 0.91 and 0.84 (each 3H, each s, 28-H$_3$, 30-H$_3$), 0.62 (3H, 18-H$_3$); $^{13}$C NMR (125 MHz, CDCl$_3$) δ 151.97 (0, C-2), 143.44 (0, C-8), 130.52 (0, C-5), 124.23 (1, C-6), 115.65 (1, C-7), 107.71 (2, =CH$_2$), 71.79 and 70.63 (each 1, C-1, C-3), 71.23 (0, C-25), 56.01 (1), 52.77 (1), 47.07 (0, C-13), 45.77 (2), 43.90 (1), 40.98 (2), 38.15 (2), 37.64 (2), 36.28 (0, C-22), 36.00 (2), 31.20 (2), 29.23 and 29.20 (each 3, C-26, C-27), 29.02 (2), 27.77 (3), 25.97 (3), 23.55 (2), 23.22 (2), 14.71 (3), 12.59 (3); MS (EI) m/z 444 (30, M$^+$), 426 (7, M$^+$−H$_2$O), 411 (2), 341 (4), 315 (20), 297 (10), 269 (12), 247 (20), 223 (4), 192 (4), 175 (6), 161 (14), 135 (40), 111 (56), 91 (100), 69 (24); MS (ESI) m/z 467 (49, [M+Na]$^+$ 911 (11, [2M+Na]$^+$), exact mass (ESI) calculated for $C_{29}H_{48}O_3Na$ [M+Na]+ 467.3501, found 467.3507.

Example 2

Synthesis of (20R)-2-methylene-19-nor-22-dimethyl-1α,25-dihydroxyvitamin D$_3$

Compounds of the present technology, including (20R)-2-methylene-19-nor-22-dimethyl-1α,25-dihydroxyvitamin D$_3$, were prepared using the methods shown in Schemes 4-6. As shown in Scheme 4, compound 4 is obtained by the same steps shown in Scheme 2 and described in Example 1. Kornblum oxidation of tosylate 4 with sodium bicarbonate in DMSO provided aldehyde 15. Compound 15 was epimerized at position 20 by treatment with tetrabutylammonium hydroxide to give compound 16 and reduced with sodium borohydride to give a mixture of diastereomers, from which compound 17, with the 20R stereochemistry, was isolated.

As shown in Scheme 5, compound 17 was subjected to an analogous series of synthetic steps to those shown in Schemes 2 and 3 to provide compound 25, the 20R diastereomer of compound 11. Likewise, as shown in Scheme 6, compound 25 was subjected to the same series of oxidation, protection, triethylphosphonoacetate condensation and deprotection steps as compound 11 in Scheme 3, to provide compound 28, (20R)-2-methylene-19-nor-22-dimethyl-1α,25-dihydroxyvitamin D$_3$. This product was fully characterized as described below.

Scheme 4

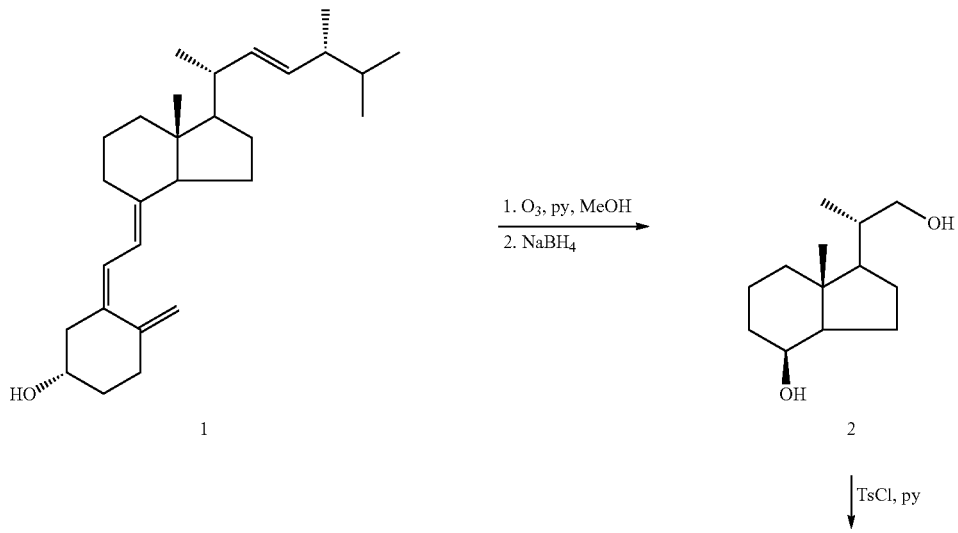

-continued
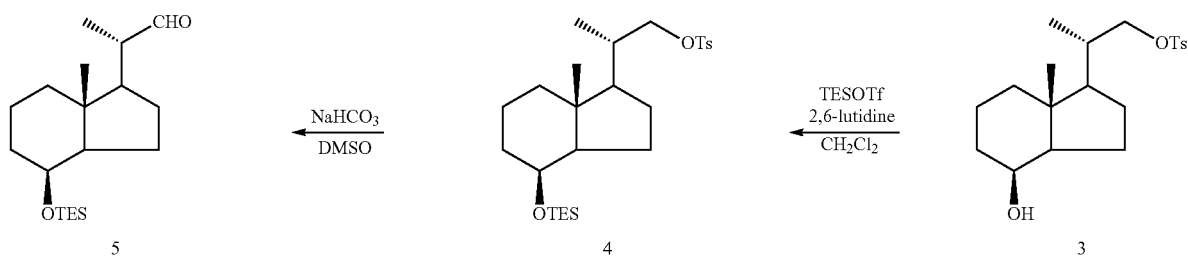
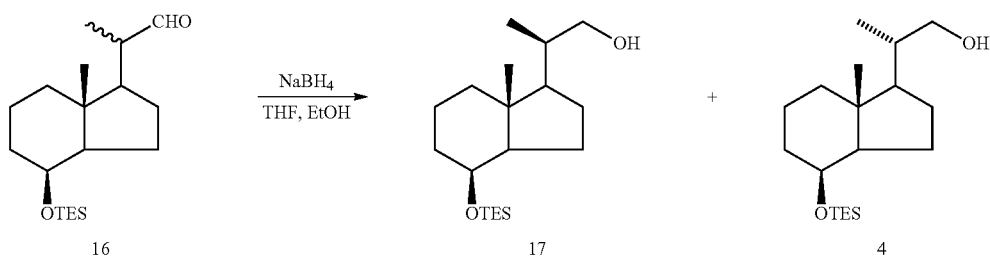
Scheme 5
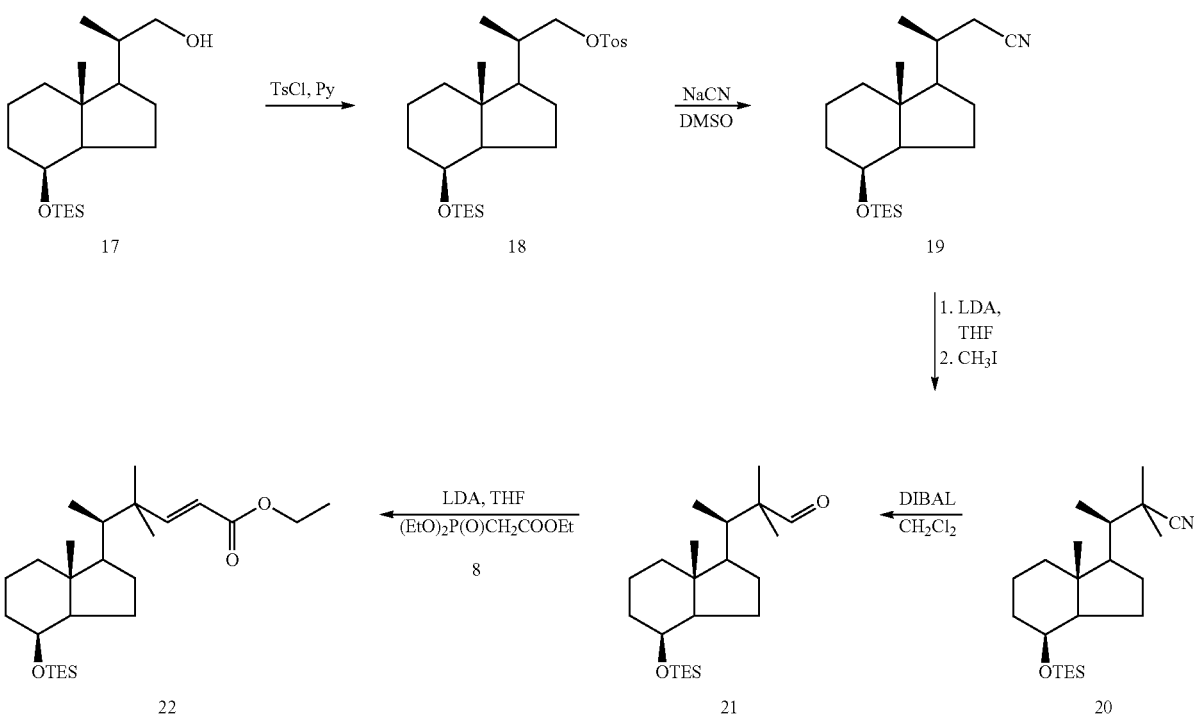

25 26

-continued

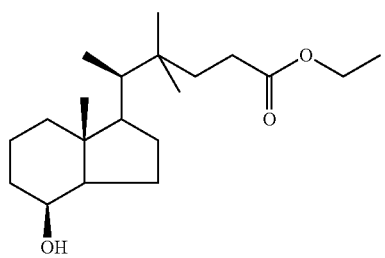
23

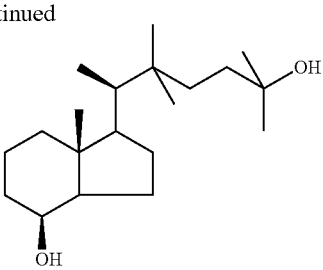
24

Scheme 6

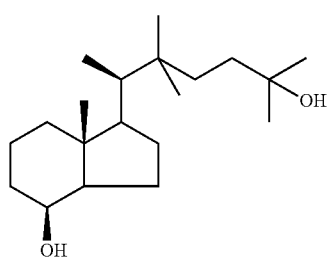
24

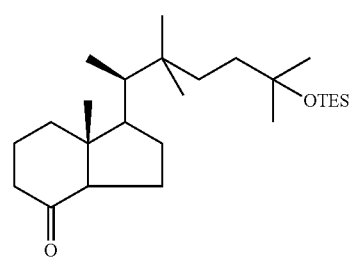
25

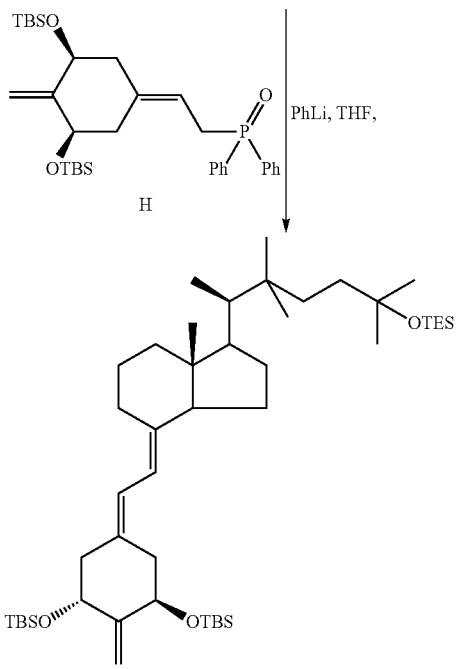

(8S,20S)-Des-A,B-8-[(triethylsilyl)oxy]-20-(formyl)-pregnane (15)

Sodium bicarbonate (5 g, 59.5 mmol) was added to a solution of tosylate 4 (2.31 g, 4.81 mmol) in DMSO (15 mL). The reaction mixture was stirred at for 1 hour 15 min 120°C. and it was diluted with ethyl acetate. The organic phase was washed with brine, dried ($Na_2SO_4$) and concentrated. The residue was purified by column chromatography on silica gel (5% ethyl acetate/hexane) to give the product 5 (1.19 g, 76% yield) as a colorless oil.

$[\alpha]_D$ +41.4 (c 1.0, $CHCl_3$); $^1$H NMR (400 MHz, $CDCl_3$) δ 9.58 (1H, d, J=3.2 Hz), 4.06 (1H, d, J=2.4 Hz), 2.36 (1H, m), 1.09 (3H, d, J=6.8, 3.0 Hz), 0.96 (3H, s), 0.94 (9H, t, J=7.9 Hz), 0.56 (6H, q, J=7.9 Hz); $^{13}$C NMR (125 MHz, $CDCl_3$) δ 205.40 (1), 69.01 (1), 52.38 (1), 51.69 (1), 49.17 (1), 42.64 (0), 40.49 (2), 34.54 (2), 26.20 (2), 23.28 (2), 17.58 (2), 13.89 (3), 13.32 (3), 6.92 (3), 4.90 (2); MS (EI) m/z 324 (5, M$^+$), 295

(100, M$^+$–EtOH), 281 (30), 246 (12), 191 (36), 175 (99), 135 (54), 103 (76); MS (ESI) m/z 671 (100, [2M+Na]$^+$), 995 (49, [3M+Na]$^+$); exact mass calculated for C$_{17}$H$_{31}$O$_2$Si [M–Et]$^+$ 295.2093, found 295.2103.

(8S,20R)-Des-A,B-8-[(triethylsilyl)oxy]-20-(hydroxymethyl)-pregnane (17)

Tetrabutylammonium hydroxide (40 wt. % solution in water, 4 mL, 3.98 g, 0.015 mol) was added to a solution of aldehyde 5 (0.97 g, 2.99 mmol) in dichloromethane (20 mL). The reaction mixture was stirred for 18 hours at room temperature and it was diluted with dichloromethane. The organic phase was washed with water, dried (Na$_2$SO$_4$) and concentrated. The product was purified by column chromatography on silica gel (3%, then 5% ethyl acetate/hexane) to give a mixture of isomers 16 (0.69 g, 71% yield). Sodium borohydride (0.2 g, 5.29 mmol) was added to a solution of aldehydes 16 (0.69 g, 2.13 mmol) in THF (10 mL) and ethanol (10 mL). The reaction mixture was stirred for 45 min., quenched with saturated NH$_4$Cl, extracted with ethyl acetate and dried (Na$_2$SO$_4$). The residue was purified by column chromatography on silica gel (4%, then 20% ethyl acetate/hexane) to give the pure isomer 17 (0.326 g, 47% yield) and a mixture of both isomers 17 and 4 (0.277 g, 40% yield).

[α]$_D$ +33.6 (c 1.0, CHCl$_3$); $^1$H NMR (500 MHz, CDCl$_3$) δ 4.03 (1H, d, J=2.5 Hz), 3.72 (1H, dd, J=10.7, 3.6 Hz), 3.44 (1H, dd, J=10.7, 7.0 Hz), 0.95 (9H, t, J=7.9 Hz), 0.94 (3H, d, J=6.6 Hz), 0.93 (3H, s), 0.55 (6H, q, J=7.9 Hz); $^{13}$C NMR (125 MHz, CDCl$_3$) δ 69.25 (1), 66.84 (2), 53.01 (1), 41.91 (0), 40.20 (2), 37.49 (1), 34.58 (2), 26.73 (2), 22.81 (2), 17.67 (2), 16.58 (3), 13.88 (3), 6.93 (3), 4.91 (2); MS (EI) m/z 326 (7, M$^+$), 311 (3, M$^+$–CH$_3$), 297 (100, M$^+$–Et), 283 (41), 265 (8), 225 (23), 193 (41), 177 (41), 135 (57), 103 (99); MS (ESI) m/z 327 (100, [M+H]$^+$); exact mass calculated for C$_{17}$H$_{33}$O$_2$Si [M–Et]$^+$ 297.2250, found 297.2244.

(8S,20R)-Des-A,B-8-[(triethylsilyl)oxy]-20-[(p-toluenesulfonyl)oxy]methyl-pregnane (18)

A solution of tosyl chloride (0.38 g, 2 mmol) in pyridine (3 mL) was transferred via cannula to a solution of alcohol 17 (0.326 g, 1 mmol) in pyridine (5 mL) at –20° C. The reaction mixture was stirred at –20° C. for 1 hour and then at +4° C. overnight. It was diluted with methylene chloride, washed with a saturated aqueous solution of CuSO$_4$ and dried (Na$_2$SO$_4$). The residue was purified by column chromatography on silica gel (5%, then 10% and 20% ethyl acetate/hexane) to give the tosylate 18 (427 mg, 89% yield) as a colorless oil.

[α]$_D$ +8.8 (c 1.0, CHCl$_3$); $^1$H NMR (400 MHz, CDCl$_3$) δ 7.78 (1H, d, J=8.2 Hz), 7.34 (1H, d, J=8.2 Hz), 4.11 (1H, dd, J=9.3, 3.4 Hz), 4.00 (1H, d, J=2.0 Hz), 3.77 (1H, dd, J=9.3, 7.4 Hz), 2.45 (3H, s), 0.93 (9H, t, J=7.9 Hz), 0.87 (3H, d, J=6.7 Hz), 0.81 (3H, s), 0.53 (6H, q, J=7.9 Hz); $^{13}$C NMR (100 MHz, CDCl$_3$) δ 144.53 (0), 133.18 (0), 129.70 (1), 127.93 (1), 74.30 (2), 69.09 (1), 52.74 (1), 52.60 (1), 41.77 (0), 39.95 (2), 34.66 (1), 34.40 (2), 26.61 (2), 22.64 (2), 21.62 (3), 17.54 (2), 16.65 (3), 13.82 (3), 6.91 (3), 4.89 (2); MS (EI) m/z 480 (18, M$^+$), 465 (2), 437 (14), 348 (2, M$^+$–Et$_3$SiOH), 309 (1, M$^+$–CH$_3$C$_6$H$_4$SO$_3$), 257 (91), 225 (23), 177 (100), 135 (19), 121 (24); MS (ESI) m/z 503 (7, [M+Na]$^+$), 983 (4, [2M+Na]$^+$), 1463 (10, [3M+Na]$^+$); exact mass calculated for C$_{26}$H$_{44}$O$_4$SSiNa [M+Na]$^+$ 503.2627, found 503.2639.

(8S,20S)-Des-A,B-8-[(triethylsilyl)oxy]-20-(cyanomethyl)-pregnane (19)

Sodium cyanide (0.9 g, 18.4 mmol) was added to a solution of tosylate 18 (0.412 g, 0.858 mmol) in DMSO (5 mL). The resulting mixture was stirred at 90° C. for 2 h, then it was cooled, diluted with water and extracted with ethyl acetate. Combined organic phases were dried (Na$_2$SO$_4$) and concentrated. The residue was purified by column chromatography on silica gel (10% ethyl acetate/hexane) to give cyanide 19 (0.242 g, 85% yield) as a colorless oil.

[α]$_D$ +17.3 (c 1.0, CHCl$_3$); $^1$H NMR (400 MHz, CDCl$_3$) δ 4.04 (1H, d, J=2.2 Hz), 2.44 (1H, dd, J=16.7, 4.0 Hz), 2.38 (1H, dd, J=16.7, 6.6 Hz), 1.06 (3H, d, J=6.7 Hz), 0.94 (9H, t, J=7.9 Hz), 0.91 (3H, s), 0.55 (6H, q, J=7.9 Hz); $^{13}$C NMR (100 MHz, CDCl$_3$) δ 118.90 (0), 69.07 (1), 54.96 (1), 52.74 (1), 41.91 (0), 40.23 (2), 34.29 (2), 31.79 (1), 27.01 (2), 24.00 (2), 22.68 (2), 19.58 (3), 17.53 (2), 13.81 (3), 6.90 (3), 4.88 (2); MS (EI) m/z 335 (3, M$^+$), 320 (1, M$^+$–Me) 306 (76, M$^+$–Et), 292 (15), 271 (2), 225 (3), 202 (30), 161 (13), 103 (100), 75 (38); MS (ESI) m/z 336 (7, [M+H]$^+$), 358 (4, [M+Na]$^+$), 693 (100, [2M+Na]$^+$), 1028 (40, [3M+Na]$^+$); exact mass calculated for C$_{18}$H$_{32}$NOSi [M–Et]$^+$ 306.2253, found 306.2253.

(8S,20R)-Des-A,B-8-[(triethylsilyl)oxy]-20-(1'-methyl-1'-cyano-ethyl)-pregnane (20)

n-Butyllithium (1.6 M in hexane, 2.4 mL, 3.8 mmol) was added to a solution of diisopropylamine (0.54 mL, 0.384 g, 3.8 mmol) in THF (2 mL) at 0° C. The resulting mixture was stirred at 0° C. for 30 min, then it was cooled to –78° C. and a solution of the compound 19 (0.326 g, 0.973 mmol) in THF (2 mL) was added. The mixture was stirred at –78° C. for 30 min and then iodomethane (1.2 mL, 2.73 g, 19.2 mmol) was added. The reaction mixture was stirred at –78° C. 1 h and then at room temperature for 1 h. It was quenched with saturated aqueous NH$_4$Cl solution and extracted with ethyl acetate. Combined organic phases were washed with brine, dried (Na$_2$SO$_4$) and concentrated. The residue was purified by column chromatography on silica gel (5%, then 10% ethyl acetate/hexane) to give the product 20 (0.197 g, 56% yield).

[α]$_D$ +30.9 (c 1.0, CHCl$_3$); $^1$H NMR (400 MHz, CDCl$_3$) δ 4.06 (1H, d, J=2.2 Hz), 1.30 (3H, s), 1.26 (3H, s), 0.97 (3H, d, J=7.1 Hz), 0.95 (9H, t, J=7.9 Hz), 0.84 (3H, s), 0.55 (6H, q, J=7.9 Hz); $^{13}$C NMR (100 MHz, CDCl$_3$) δ 126.16 (0), 68.91 (1), 52.01 (1), 50.84 (1), 42.88 (0), 37.84 (1), 37.77 (2), 34.88 (2), 24.97 (3), 23.88 (3), 23.17 (2), 21.81 (2), 17.36 (2), 14.54 (3), 13.03 (3), 6.92 (3), 4.90 (2); MS (EI) m/z 363 (13, M$^+$), 334 (72, M$^+$–Et), 320 (12), 295 (4), 261 (4), 249 (15), 234 (29), 191 (100), 163 (72), 111 (81), 93 (28), 81 (39), 57 (49); MS (EI) m/z 363 (12, M$^+$), 334 (71), 320 (12), 295 (4), 234 (28), 191 (100), 163 (71), 135 (42), 111 (80); MS (ESI) m/z 364 (11, [M+H]$^+$), 749 (62, [2M+Na]$^+$), 1113 (100, [3M+Na+H]$^{2+}$); exact mass calculated for C$_{22}$H$_{42}$ONSi [M+H]$^+$ 364.3031, found 364.3044.

(8S,20R)-Des-A,B-8-[(triethylsilyl)oxy]-20-(1'-methyl-1'-formyl-ethyl)-pregnane (21)

Diisobutylaluminium hydride (1.0 M in dichloromethane, 3.1 mL, 3.1 mmol) was added to a solution of the compound 20 (0.197 g, 0.543 mmol) in dichloromethane (4 mL) at –10° C. The reaction mixture was stirred at –10° C. for 1 hour, then it was quenched with a saturated aqueous sodium potassium tartrate solution (5 mL). The water phase was extracted with dichloromethane. Combined organic layers were washed with brine and dried (Na$_2$SO$_4$) and concentrated. The residue was purified on Sep-Pak cartridge (5 g). The cartridge was washed with hexane/ethyl acetate (9:1) to give the aldehyde 21 as colorless oil (0.15 g, 75% yield).

[α]$_D$ +35.0 (c 1.0, CHCl$_3$). $^1$H NMR (400 MHz, CDCl$_3$) δ 9.40 (1H, s), 4.04 (1H, d, J=2.2 Hz), 0.95 (6H, s), 0.94 (9H, t, J=7.8 Hz), 0.85 (3H, d, J=7.00 Hz), 0.85 (3H, s), 0.55 (6H, q, J=7.8 Hz); $^{13}$C NMR (100 MHz, CDCl$_3$) δ 207.49 (1), 68.91 (1), 51.96 (1), 50.79 (1), 50.68 (0), 42.89 (0), 38.34 (2), 34.88 (2), 33.78 (1), 23.18 (2), 22.13 (2), 19.41 (3), 18.09 (3), 17.40 (2), 14.48 (3), 12.29 (3), 6.92 (3), 4.90 (2); MS (EI) m/z 366 (1, M$^+$), 337 (31, M$^+$-Et), 307 (37), 295 (12), 251 (13), 225 (30), 203 (22), 186 (9), 171 (14), 163 (74), 135 (43), 103 (100); MS (ESI) m/z 389 (29, [M+Na]$^+$), 755 (73, [2M+Na]$^+$), 1121 (15, [3M+Na]$^+$); exact mass (ESI) calculated for C$_{22}$H$_{42}$O$_2$SiNa [M+Na]$^+$ 389.2847, found 389.2838.

(8S,20R)-Des-A,B-8-[(triethylsilyl)oxy]-20-(1'-dimethyl-3'-ethyloxycarbonyl-2'-propenyl)-pregnane (22)

n-Butyllithium (1.6 M in hexane, 5.2 mL, 8.3 mmol) was added to a solution of diisopropylamine (1.2 mL, 0.840 g, 8.3 mmol) in dry THF (2 mL) at 0° C. After 30 min the mixture was cooled to −10° C. and triethylphosphonoacetate 8 (1.9 mL, 2.13 g, 9.5 mmol) was added. The reaction mixture was stirred at −10° C. for 30 min and a solution of the aldehyde 21 (0.15 g, 0.41 mmol) in anhydrous THF (5 mL+3 mL) was added via cannula. The mixture was stirred under argon at −10° C. for 1 h, then it was heated to +37° C. for 3 h and later it was stirred at room temperature for 18 h. Dichloromethane was added and the organic phase was washed with water, dried (Na$_2$SO$_4$) and concentrated. The product was purified on Sep-Pak cartridge (5 g). The cartridge was washed with hexane/ethyl acetate (2%, then 3% and 5%) to give the product 22 (99 mg, 55% yield) as a colorless oil. [α]$_D$ +18.1 (c 1.0, CHCl$_3$); $^1$H NMR (400 MHz, CDCl$_3$) δ 6.92 (1H, d, J=15.9 Hz), 5.69 (1H, d, J=15.9 Hz), 4.19 (2H, m), 4.03 (1H, d, J=2.0 Hz), 1.29 (3H, t, J=7.1 Hz), 0.98 (3H, s), 0.96 (3H, s), 0.94 (9H, t, J=7.9 Hz), 0.81 (3H, d, J=7.0 Hz), 0.80 (3H, s), 0.54 (6H, q, J=7.9 Hz); $^{13}$C NMR (100 MHz, CDCl$_3$) δ 167.19 (0), 159.65 (1), 117.69 (1), 69.04 (1), 60.07 (2), 52.08 (1), 50.18 (1), 42.83 (0), 41.16 (0), 38.53 (1), 38.19 (2), 35.00 (2), 24.64 (3), 23.30 (3), 22.14 (2), 17.49 (2), 14.50 (3), 14.29 (3), 13.02 (3), 6.94 (3), 4.93 (2); MS (EI) m/z 436 (0.3, M$^+$), 407 (3, M$^+$-Et), 334 (2), 286 (10), 257 (18), 229 (100), 206 (16), 191 (99), 163 (26), 142 (16); MS (ESI) m/z 459 (99, [M+Na]$^+$), 896 (100, [2M+Na+H]$^{2+}$), 1332 (47, [3M+Na+H]$^{2+}$), exact mass (ESI) calculated for C$_{26}$H$_{48}$O$_3$SiNa [M+Na]$^+$ 459.3265, found 459.3259.

(8S,20R)-Des-A,B-20-(1'-dimethyl-3'-ethyloxycarbonyl-propyl)-pregnan-8-ol (23)

A solution of the ester 22 (99 mg, 0.23 mmol) in methanol (5 mL) was hydrogenated in the presence of 10% palladium on powdered charcoal (10 mg) at room temperature for 20 h. The reaction mixture was filtered through a Waters silica Sep-Pak cartridge (2 g), which was further washed with methanol. After removal of the solvent the ester 23 (50.4 mg, 68%) was obtained as a colorless oil.

[α]$_D$ +15.3 (c 1.0, CHCl$_3$). $^1$H NMR (400 MHz, CDCl$_3$) δ 4.12 (2H, q, J=7.1 Hz), 4.09 (1H, s), 2.25 (3H, m), 1.26 (3H, t, J=7.1 Hz), 0.85 (3H, s), 0.80 (3H, s), 0.79 (3H, d, J=7.6 Hz), 0.78 (3H, s); $^{13}$C NMR (100 MHz, CDCl$_3$) δ 174.60 (0), 69.07 (1), 60.21 (2), 51.69 (1), 49.40 (1), 42.60 (0), 37.93 (2), 37.07 (1), 36.04 (0), 34.57 (2), 33.92 (2), 29.54 (2), 24.82 (3), 24.56 (3), 22.90 (2), 22.26 (2), 17.26 (2), 14.49 (3), 14.20 (3), 12.62 (3); MS (EI) m/z 324 (3, M$^+$), 278 (7), 261 (8), 224 (7), 210 (5), 181 (15), 163 (70), 143 (100), 129 (33), 111 (72), 97 (44), 69 (48); MS (ESI) m/z 342 (100, [M+NH$_4$]$^+$), 671 (11, [2M+Na]$^+$), exact mass calculated for C$_{20}$H$_{37}$O$_3$ [M+H]$^+$ 325.2738, found 325.2727.

(8S,20R)-Des-A,B-22-dimethyl-cholestan-8,25-diol (24)

Methylmagnesium bromide (3.0 M solution in diethyl ether, 130 μL, 0.39 mmol) was added to a solution of the ester 23 (50 mg, 0.154 mmol) in anhydrous diethyl ether (3 mL) at 0° C. The reaction mixture was stirred at 0° C. for 2 h and then at room temperature for 18 h. It was quenched with a saturated aqueous NH$_4$Cl solution, extracted with ethyl acetate, dried (Na$_2$SO$_4$) and concentrated. The residue was applied to a Waters silica Sep-Pak cartridge (5 g). Elution with ethyl acetete/hexane (1:1) gave the diol 24 (48 mg, 100%) as colorless crystals. m.p. 122-124° C. (from ethyl acetate/hexane); [α]$_D$ +21.2 (c 0.988, CHCl$_3$). $^1$H NMR (400 MHz, CDCl$_3$) δ 4.10 (1H, d, J=1.8 Hz), 1.21 (6H, s), 0.85 (3H, s), 0.81 (3H, s), 0.78 (3H, d, J=7.3 Hz), 0.76 (3H, s); $^{13}$C NMR (100 MHz, CDCl$_3$) δ 71.15 (0), 69.13 (1), 51.71 (1), 49.44 (1), 42.62 (0), 38.06 (2), 37.73 (2), 36.96 (1), 35.90 (0), 34.17 (2), 33.92 (2), 29.24 (3), 29.15 (3), 25.38 (3), 24.81 (3), 22.94 (2), 22.36 (2), 17.27 (2), 14.50 (3), 12.62 (3); MS (EI) m/z 292 (5, M$^+$-H$_2$O), 223 (3), 205 (9), 163 (43), 149 (9), 135 (21), 129 (41), 111 (100), 95 (25), 81 (20); MS (ESI) m/z 310 (84, [M]$^+$), 328 (88, [M+NH$_4$]$^+$), 643 (24, [2M+Na]$^+$), exact mass (ESI) calculated for naC$_{20}$H$_{38}$O$_2$Na [M+Na]$^+$ 333.2765, found 333.2764.

(20R)-Des-A,B-22-dimethyl-25-[(triethylsilyl)oxy]-cholestan-8-one (25)

Molecular sieves A4 (100 mg) were added to a solution of 4-methylmorpholine oxide (90 mg, 0.77 mmol) in dichloromethane (400 μL). The mixture was stirred at room temperature for 15 min and tetrapropylammonium perruthenate (9.7 mg, 27.6 μmol) was added, followed by a solution of diol 24 (29.4 mg, 0.095 mmol) in dichloromethane (300+100 μL). The resulting suspension was stirred at room temperature for 1 h. The reaction mixture was filtered through a Waters silica Sep-Pak cartridge (2 g) that was further washed with ethyl acetate. After removal of the solvent the ketone (29.5 mg) was obtained as a colorless oil.

Triethylsilyl trifluoromethanesulfonate (30 μL, 35.1 mg, 0.133 mmol) was added dropwise to a solution of the ketone (29.2 mg, 0.095 mmol) and 2,6-lutidine (40 μL, 37 mg, 0.343 mmol) in dichloromethane (1.6 mL) at −50° C. The reaction mixture was stirred at −40° C. for 15 min, then it was diluted with dichloromethane and washed with water. The organic layer was dried (Na$_2$SO$_4$) and concentrated. The residue was applied to a Waters silica Sep-Pak cartridge (5 g). Elution with hexane/ethyl acetate (1%, then 2%) gave the protected ketone 25 (34.4 mg, 86% yield).

[α]$_D$ −8.8 (c 1.0, CHCl$_3$). $^1$H NMR (400 MHz, CDCl$_3$) δ 2.44 (1H, dd, J=11.5, 7.5 Hz), 1.20 (6H, s), 0.95 (9H, t, J=7.9 Hz), 0.82 (3H, s), 0.79 (3H, d, J=7.5 Hz), 0.78 (3H, s), 0.58 (3H, s), 0.57 (6H, q, J=7.9 Hz); $^{13}$C NMR (100 MHz, CDCl$_3$) δ 212.18 (0), 73.42 (0), 60.66 (1), 51.10 (0), 49.73 (1), 41.01 (2), 38.88 (2), 38.26 (1), 36.76 (2), 35.95 (0), 33.93 (2), 29.89 (3), 25.17 (3), 24.91 (3), 23.66 (2), 22.68 (2), 19.47 (2), 12.99 (3), 12.33 (3), 7.14 (3), 6.82 (2); MS (EI) m/z no M$^+$, 407 (33), 393 (68), 364 (54), 323 (11), 293 (25), 253 (42), 173 (82), 163 (70), 111 (78), 107 (100); MS (ESI) m/z 423 (27, [M+H]$^+$), 445 (47, [M+Na]$^+$), 867 (26, [2M+Na]$^+$), 1290 (8, [3M+Na+H]$^{2+}$), exact mass (ESI) calculated for C$_{26}$H$_{51}$O$_2$Si [M+H]$^+$ 423.3653, found 423.3649.

(20R)-2-Methylene-19-nor-22-dimethyl-1α,25-dihydroxyvitamin D$_3$ (27)

Phenyllithium (1.70 M in di-n-buthylether, 105 μL, 0.178 mmol) was added to a stirred solution of the phosphine oxide H (73.6 mg, 0.126 mmol) in anhydrous THF (500 μL) at −30° C. After 30 min the mixture was cooled to −78° C. and a precooled (−78° C.) solution of the ketone 25 (35 mg, 82.9 μmol) in anhydrous THF (400+300 μL) was added. The reaction mixture was stirred under argon at −78° C. for 4 hours and then at +4° C. for 19 h. Ethyl acetate was added and the organic phase was washed with brine, dried (Na$_2$SO$_4$) and concentrated. The residue was applied to a Waters silica Sep-Pak cartridge (5 g). The cartridge was washed with hexane and ethyl acetate/hexane (1:99) to give the crude product. The vitamin was further purified by straight phase HPLC [9.4×250 mm Zorbax Silica column, 4 mL/min, hexane/2-propanol (0.1%) solvent system, R$_f$=3.2 min.] to give the pure protected compound 26 (51.09 mg, 78% yield).

UV (in hexane) λ$_{max}$ 262.5, 252.5, 244.5 nm; $^1$H NMR (400 MHz, CDCl$_3$) δ 6.22 (1H, d, J=11.1 Hz, 6-H), 5.84 (1H, d, J=11.1 Hz, 7-H), 4.97 (1H, s, =CH$_2$), 4.92 (1H, s, =CH$_2$), 4.42 (2H, m, 1β-H and 3α-H), 2.85 (1H, dd, J=12.8, 3.6 Hz, 9β-H), 2.52 (1H, dd, J=13.2, 6.0 Hz, 10α-H), 2.46 (1H, dd, J=12.6, 4.3 Hz, 4α-H), 2.34 (1H, dd, J=13.2, 2.7 Hz, 10β-H), 2.18 (1H, dd, J=12.6, 8.4 Hz, 4β-H), 1.96 (1H, m), 1.19 (6H, s, 26-H$_3$, 27-H$_3$), 0.95 (9H, t, J=7.9 Hz), 0.897 (9H, s, t-BuSi), 0.866 (9H, s, t-BuSi), 0.80 and 0.77 (each 3H, each s, 28-H$_3$, 30-H$_3$), 0.79 (3H, d, J=8.2 Hz, 21-H$_3$), 0.57 (6H, q, J=7.9 Hz), 0.46 (3H, s, 18-H$_3$), 0.080 (3H, s, SiMe), 0.069 (3H, s, SiMe), 0.049 (3H, s, SiMe), 0.029 (3H, s, SiMe); $^{13}$C NMR (100 MHz, CDCl$_3$) δ 152.98 (0, C-2), 141.35 (0, C-8), 132.64 (0, C-5), 122.44 (1, C-6), 115.77 (1, C-7), 106.24 (2, =CH$_2$), 73.51 (0, C-25), 72.50 and 71.64 (each 1, C-1, C-3), 55.06 (1), 49.61 (1), 47.59 (2), 46.71 (0, C-13), 38.92 (2), 38.55 (2), 38.29 (2), 38.09 (1), 35.96 (0, C-22), 34.08 (2), 29.93 and 29.88 (each 3, C-26, C-27), 28.93 (2), 25.84 (3), 25.77 (3), 25.25 (3), 25.02 (3), 23.05 (2), 22.68 (2), 22.63 (2), 18.26 (0), 18.17 (0), 12.81 (3), 12.44 (3), 7.16 (3), 6.84 (2), −4.86 (3), −4.91 (3), −5.08 (3); MS (ESI) m/z 809 (40, [M+Na]$^+$), exact mass (ESI) calculated for C$_{47}$H$_{90}$O$_3$Si$_3$Na [M+Na]+ 809.6091, found 809.6101.

The protected compound 26 (50.94 mg, 64.8 mol) was dissolved in THF (5 mL) and acetonitrile (3 mL). A solution of aqueous 48% HF in acetonitrile (1:9 ratio, 4 mL) was added at 0° C. and the resulting mixture was stirred at room temperature for 2 h. Saturated aqueous NaHCO$_3$ solution was added and the reaction mixture was extracted with dichloromethane. The combined organic phases were dried (Na$_2$SO$_4$) and concentrated under reduced pressure. The residue was diluted with 2 mL of hexane/ethyl acetate (7:3) and applied to a Waters silica Sep-Pak cartridge (5 g). An elution with hexane/ethyl acetate (7:3, then 1:1) gave the crude product 20. The vitamin 20 was further purified by straight phase HPLC [9.4×250 mm Zorbax Silica column, 4 mL/min, hexane/2-propanol (85:15) solvent system, R$_f$=7.4 min.] and reverse phase HPLC [9.4×250 mm Zorbax RX-C18 column, 3 mL/min, methanol/water (85:15) solvent system, R$_f$=13.3 min.] to give the pure compound 27 (22.71 mg, 79% yield).

m.p. 154° C. (from 2-propanol/hexane); UV (in EtOH) λ$_{max}$ 261.0, 252.0, 244.0 nm; $^1$H NMR (500 MHz, CDCl$_3$) δ 6.35 (1H, d, J=11.2 Hz, 6-H), 5.88 (1H, d, J=11.2 Hz, 7-H), 5.11 (1H, s, =CH$_2$), 5.08 (1H, s, =CH$_2$), 4.48 (2H, m, 1(3-H and 3α-H), 2.86 (1H, dd, J=13.0, 4.7 Hz, 10β-H), 2.84 (1H, m, 9β-H), 2.56 (1H, dd, J=13.3, 3.5 Hz, 4α-H), 2.33 (1H, dd, J=13.3, 6.0 Hz, 4β-H), 2.28 (1H, dd, J=13.0, 8.4 Hz, 10α-H), 1.96 (2H, m), 1.88 (1H, m), 1.21 (6H, s, 26-H$_3$, 27-H$_3$), 0.83 and 0.78 (each 3H, each s, 28-H$_3$, 30-H$_3$), 0.79 (3H, d, J=7.4 Hz, 21-H$_3$), 0.48 (3H, 18-H$_3$); $^{13}$C NMR (125 MHz, CDCl$_3$) δ 151.98 (0, C-2), 143.27 (0, C-8), 130.51 (0, C-5), 124.09 (1, C-6), 115.02 (1, C-7), 107.66 (2, =CH$_2$), 71.74 and 70.51 (each 1, C-1, C-3), 71.23 (0, C-25), 55.05 (1), 49.52 (1), 46.81 (0, C-13), 45.70 (2), 38.10 (2×2), 37.73 (1 and 2), 35.95 (0, C-22), 34.17 (2), 29.20 (3), 29.13 (3), 29.06 (2), 25.35 (3), 24.83 (3), 23.05 (2), 22.65 (2×2), 12.82 (3), 12.41 (3); MS (EI) m/z 444 (6, M$^+$), 426 (3, M$^+$+H$_2$O), 393 (2), 341 (2), 313 (6), 269 (5), 251 (6), 199 (6), 191 (15), 161 (10), 145 (19), 111 (43), 107 (100), 89 (80), 79 (78), 75 (43); MS (ESI) m/z 467 (100, [M+Na]$^+$), 911 (55, [2M+Na]$^+$), 1355 (15, [3M+Na]$^+$, exact mass (ESI) calculated for C$_{29}$H$_{48}$O$_3$Na [M+Na]$^+$ 467.3496, found 467.3483.

Example 3

Biological Activity

Vitamin D Receptor Binding

Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in TEDK$_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 (OH)$_2$D$_3$: molar extinction coefficient=18,200 and λ$_{max}$=265 nm; Analogs: molar extinction coefficient=42,000 and λ$_{max}$=252 nm). Radiolabeled ligand ($^3$H-1,25(OH)$_2$D$_3$, ~159 Ci/mmole) was added in ethanol at a final concentration of 1 nM.

Assay Conditions

Radiolabeled and unlabeled ligands were added to 100 μL of the diluted protein at a final ethanol concentration of ≤10%, mixed and incubated overnight on ice to reach binding equilibrium. The following day, 100 μL of hydroxylapatite slurry (50%) was added to each tube and mixed at 10-minute intervals for 30 minutes. The hydroxylapatite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 mL of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≤0.2%) present in the cell cultures.
Cells Human promyelocytic leukemia (HL60) cells were grown in RPMI-1640 medium containing 10% fetal bovine serum. The cells were incubated at 37° C. in the presence of 5% $CO_2$.
Assay Conditions HL60 cells were plated at $1.2\times10^5$ cells/mL. Eighteen hours after plating, cells in duplicate were treated with drug. Four days later, the cells were harvested and a nitro blue tetrazolium reduction assay was performed (Collins et al., *J. Exp. Med.* (1979) 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24-Ohase) gene promoter upstream of a luciferase reporter gene (Arbour et al., *Analytical Biochem.* (1998) 255(1):148-154). Cells were given a range of doses. Sixteen hours after dosing the cells were harvested and luciferase activities were measured using a luminometer. RLU=relative luciferase units.

Intestinal Calcium Transport and Bone Calcium Mobilization

Figure 3:
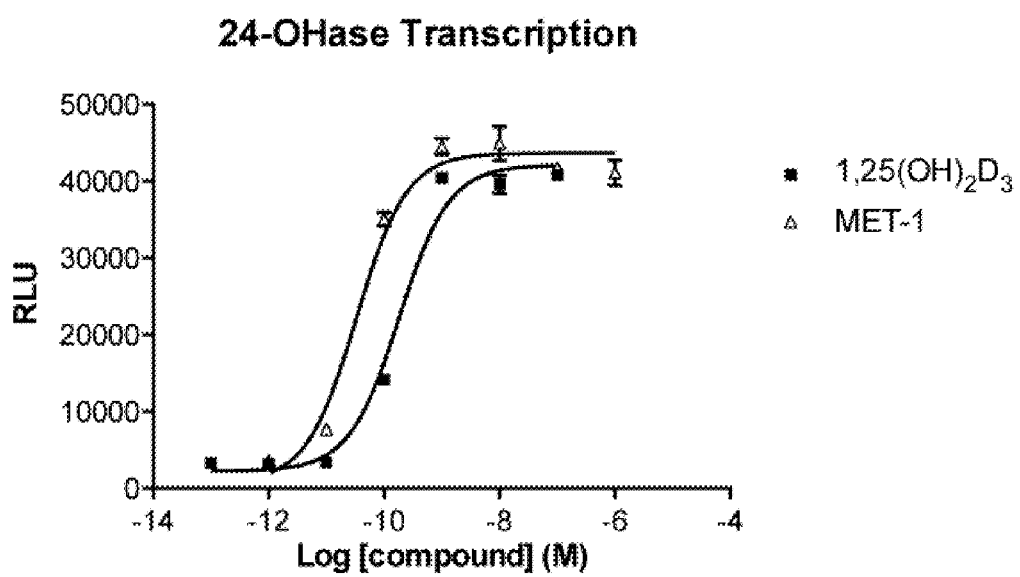
Figure 5:
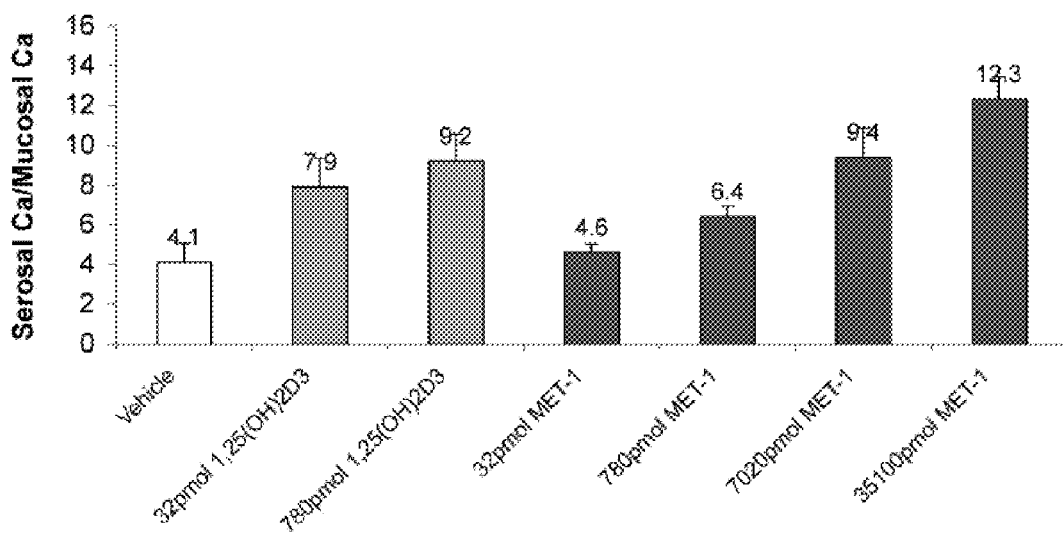

Male, weanling Sprague-Dawley rats were placed on Diet 11 (0.47% Ca) diet+AEK oil for one week followed by Diet 11 (0.02% Ca)+AEK oil for 3 weeks. The rats were then switched to a diet containing 0.47% Ca for one week followed by two weeks on a diet containing 0.02% Ca. Dose administration began during the last week on 0.02% calcium diet. Four consecutive intraperitoneal doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.
Biological Activity Results (20S)-2-methylene-19-nor-22-dimethyl-1α,25-dihydroxyvitamin $D_3$ (MET-1) is approximately equally effective as 1,25-$(OH)_2D_3$ in binding to the recombinant vitamin D receptor as shown in FIG. 1 ($K_i$ of $4\times10^{-11}$M and $5\times10^{-11}$ M respectively). However, MET-1 is 4 times more potent than 1,25-$(OH)_2D_3$ at inducing the differentiation of HL-60 cells in culture as shown in FIG. 2 ($7\times10^{-10}$M and $3\times10^{-9}$M respectively). MET-1 is 10 times as potent in stimulating 24-OHase gene expression in bone cells than 1,25-$(OH)_2D$ as shown in FIG. 3 ($3\times10^{-11}$M and $2\times10^{-10}$M respectively). By contrast, in vivo testing demonstrated that MET-1 is 20 times less active than 1,25-$(OH)_2D_3$ on bone calcium mobilization (FIG. 4), and noticeably less active than 1,25-$(OH)_2D_3$ in causing intestinal calcium transport (FIG. 5).

Figure 6:
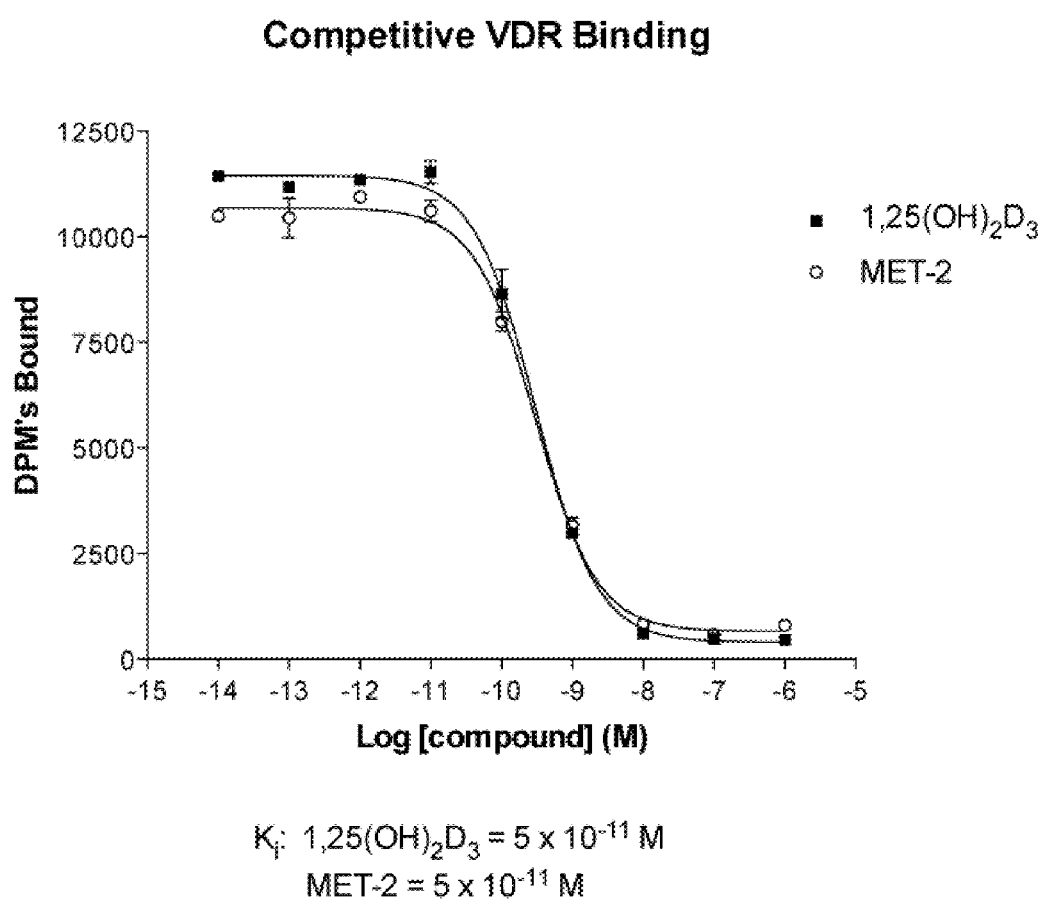
FIGS. 6-10 illustrate various biological activities of (20R)-2-methylene-19-nor-22-dimethyl-1α,25-dihydroxyvitamin $D_3$ (referred to as "MET-2" in the figures) compared with those of the native hormone, 1,25(OH)$_2$D$_3$.
Figure 8:
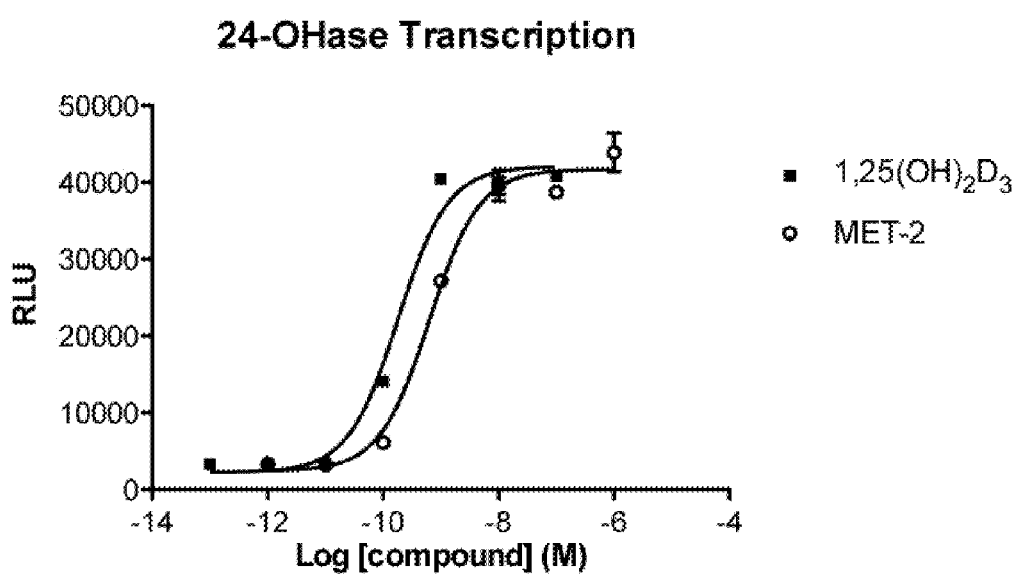

(20R)-2-methylene-19-nor-22-dimethyl-1α,25-dihydroxyvitamin $D_3$ (MET-2) is equally effective as 1,25-$(OH)_2D_3$ in binding to the recombinant vitamin D receptor as shown in FIG. 6 (both display a $K_i$ of $5\times10^{-11}$M). MET-2 is 3 times more potent than 1,25-$(OH)_2D_3$ at inducing the differentiation of HL-60 cells in culture as shown in FIG. 7 ($7\times10^{-10}$M and $3\times10^{-9}$M respectively). However, MET-2 is about 3 times less potent in stimulating 24-OHase gene expression in bone cells than 1,25-$(OH)_2D$ as shown in FIG. 8 ($3\times10^{-11}$M and $2\times10^{-10}$M respectively). In vivo testing demonstrated that MET-2 is 16 times less active than 1,25-$(OH)_2D_3$ on bone calcium mobilization (FIG. 4), and noticeably less active than 1,25-$(OH)_2D_3$ in causing intestinal calcium transport (FIG. 5).

Comparative Example

Table 1 shows biological data for 2-methylene-19-nor-1α,25-dihydroxyvitamin $D_3$ and its 20R isomer in comparison to compounds from the present disclosure (MET-1 and MET-2). The former compounds differ from the latter in that they have two methyl groups attached to the position 21 carbon rather than two hydrogens. While binding of the vitamin D receptor and HL-50 differentiation is generally within an order of magnitude for each compound, the present compounds demonstrate surprising and unexpected effects on calcemic activity. Whereas the 2MD compounds show extremely potent net bone calcium mobilization activity ranging from 4.5 mg/dL in the 20R isomer to 9.3 mg/dL in the 20S isomer, the present MET compounds show virtually no calcemic activity. On the other hand, while the 2 MD compounds demonstrate intestinal calcemic activity lower than that of vehicle, but the present compounds show small but significant ratio of serosal to mucosal calcium, i.e., 1.2 to 2.3 for MET-2 and MET-1, respectively.

These properties illustrate that both compounds should be very useful in the treatment of diseases where a rise in serum calcium is not desirable. Thus, these compounds should find utility in the treatment of secondary hyperparathyroidism of patients suffering from chronic kidney failure because it is undesirable to elevate serum calcium above normal in these patients for fear of calcification of heart, aorta and other vital organs while suppressing parathyroid gland proliferation and transcription of the preproparathyroid gene. Likewise, these compounds should be useful in the treatment of malignancy such as breast, colorectal and prostate cancers, or in the treatment of autoimmune diseases such as multiple sclerosis, lupus, rheumatoid arthritis, type 1 diabetes, and inflammatory bowel disease. They should also be useful in preventing transplant rejection.

TABLE 1

| Example* | Where | Side chain | Competitive VDR Binding ($K_i$, nM) | HL-60 Differentiation ($EC_{50}$, nM) | 24-OHase Transcription ($EC_{50}$, nM) | Net Bone $Ca^{2+}$ Mobilization (mg/dL)[1] | Net Intestinal $Ca^{2+}$ Transport (S/M)[2] |
|---|---|---|---|---|---|---|---|
| MET-1 | Present | | 0.04 | 0.7 | 0.03 | 0.4 | 2.3 |
| MET-2 | Present | | 0.05 | 1 | 0.6 | 0.2 | 1.2 |
| 2MD[3] (20R) | U.S. Pat. No. 5,843,928 | | 0.12 | 4.2 | — | 4.5[4] | −0.6[4] |
| 2MD[3] (20S) | U.S. Pat. No. 5,843,928 | | 0.10 | 0.15 | — | 9.3[4] | −0.9[4] |

*All compounds are 2-methylene-19-nor compounds
[1]At 780 pM dosage, except where indicated
[2]S/M = serosal $Ca^{2+}$/mucosal $Ca^{2+}$; at 780 pM dosage, except where indicated
[3]data from U.S. Pat. No. 5,843,928 and *J. Med. Chem.* 1998, 41, 4662
[4]At 260 pM dosage It is understood that the present technology is not limited to the embodiments set forth herein for illustration, but embraces all such forms thereof as come within the scope of the following claims.

What is claimed is:

1. A compound according to formula I:

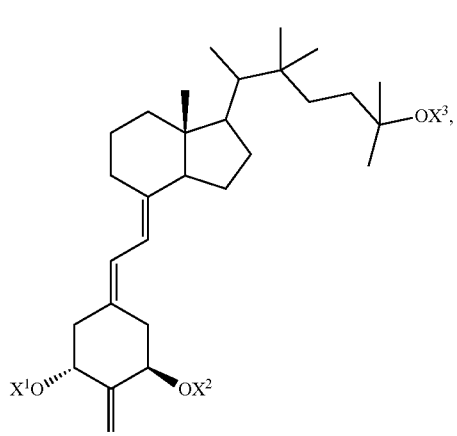

wherein $X^1$, $X^2$ and $X^3$ are independently selected from H and hydroxy protecting groups.

2. The compound of claim 1, wherein $X^1$ and $X^2$ are both hydroxy protecting groups.

3. The compound of claim 2, wherein $X^1$ and $X^2$ are both t-butyldimethylsilyl groups and $X^3$ is a triethylsilyl group.

4. A compound according to formula II:

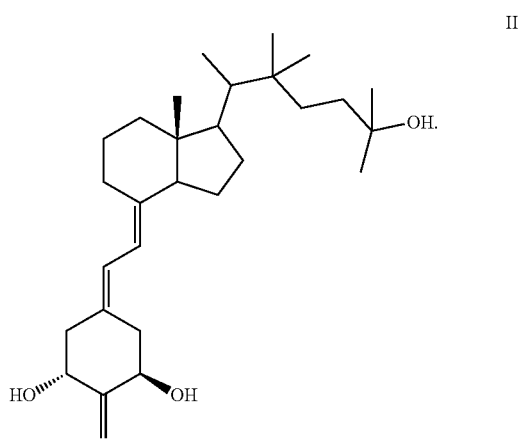

5. The compound of claim 4 according to formula IIA:

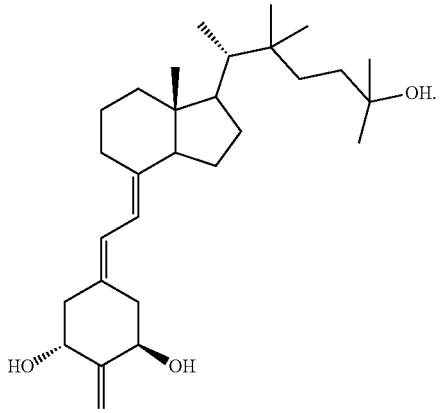

IIA

6. The compound of claim 4 according to formula IIB:

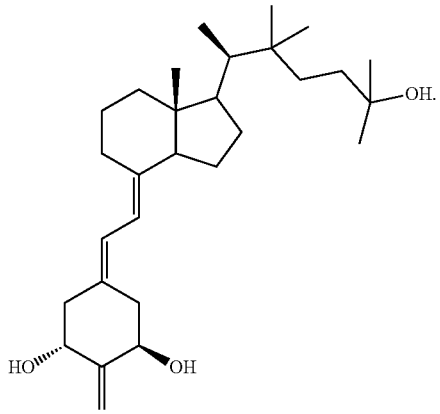

IIB

7. The compound of claim 4, according to formula IIC or IID

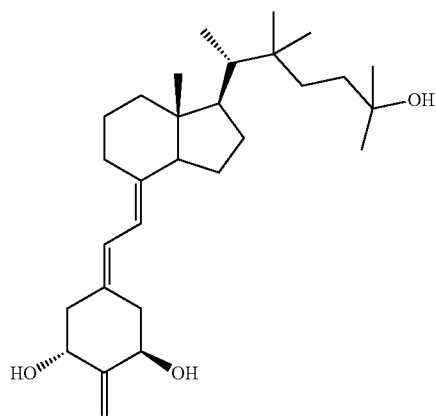

IIC

-continued

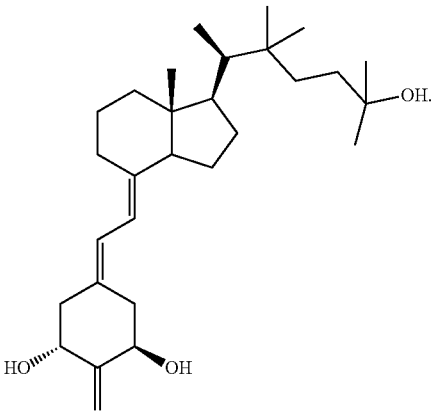

IID

8. A pharmaceutical composition, comprising an effective amount of the compound of claim 4 and a pharmaceutically acceptable carrier.

9. The pharmaceutical composition of claim 8 wherein the effective amount comprises from about 0.01 μg to about 1 mg of the compound per gram of the composition.

10. The pharmaceutical composition of claim 8 wherein the effective amount comprises from about 0.1 μg to about 500 μg of the compound per gram of the composition.

11. A method of treating a subject suffering from a biological condition, comprising administering an effective amount of the compound of claim 4 to the subject, wherein the biological condition is selected from psoriasis; leukemia; colon cancer; breast cancer; prostate cancer; multiple sclerosis; lupus; diabetes mellitus; host versus graft reaction; rejection of organ transplants; an inflammatory disease selected from rheumatoid arthritis, asthma, or inflammatory bowel diseases; a skin condition selected from wrinkles, lack of adequate skin firmness, lack of adequate dermal hydration, or insufficient sebum secretion; renal osteodystrophy; or osteoporosis.

12. The method of claim 11, wherein the biological condition is psoriasis.

13. The method of claim 11, wherein the biological condition is selected from leukemia, colon cancer, breast cancer, or prostate cancer.

14. The method of claim 11, wherein the biological condition is selected from multiple sclerosis, lupus, diabetes mellitus host versus graft reaction, or rejection of organ transplants.

15. The method of claim 11, wherein the biological condition is selected from rheumatoid arthritis, asthma, or inflammatory bowel diseases selected from celiac disease, ulcerative colitis and Crohn's disease.

16. The method of claim 11, wherein the biological condition is selected from wrinkles, lack of adequate skin firmness, lack of adequate dermal hydration, or insufficient sebum secretion.

17. The method of claim 11, wherein the compound is administered orally to the subject.

18. The method of claim 11, wherein the compound is administered parenterally to the subject.

19. The method of claim 11, wherein the compound is administered transdermally or topically to the subject.

20. The method of claim 11, wherein the compound is administered in a dosage of from 0.01 μg per day to 1 mg per day.

* * * * *